United States Patent
Morikawa et al.

(10) Patent No.: US 9,232,904 B2
(45) Date of Patent: Jan. 12, 2016

(54) ELECTROENCEPHALOGRAM RECORDING APPARATUS, HEARING AID, ELECTROENCEPHALOGRAM RECORDING METHOD, AND PROGRAM THEREOF

(71) Applicant: Panasonic Corporation, Osaka (JP)

(72) Inventors: Koji Morikawa, Kyoto (JP); Jun Ozawa, Nara (JP); Shinobu Adachi, Nara (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 324 days.

(21) Appl. No.: 13/746,041

(22) Filed: Jan. 21, 2013

(65) Prior Publication Data

US 2013/0138012 A1 May 30, 2013

Related U.S. Application Data

(63) Continuation of application No. PCT/JP2012/000308, filed on Jan. 19, 2012.

(30) Foreign Application Priority Data

Feb. 10, 2011 (JP) ................................. 2011-026974

(51) Int. Cl.
*A61B 5/04* (2006.01)
*H04R 25/00* (2006.01)
(Continued)

(52) U.S. Cl.
CPC ........... *A61B 5/04845* (2013.01); *A61B 5/0482* (2013.01); *A61B 5/125* (2013.01);
(Continued)

(58) Field of Classification Search
None
See application file for complete search history.

(56) References Cited

U.S. PATENT DOCUMENTS

2001/0049480 A1 12/2001 John et al.
2002/0051549 A1* 5/2002 Uvacek et al. ................ 381/312
(Continued)

FOREIGN PATENT DOCUMENTS

CN 101015451 A 8/2007
CN 101783998 A 7/2010
(Continued)

OTHER PUBLICATIONS

International Search Report for corresponding International Application No. PCT/JP2012/000308 mailed Mar. 19, 2012.
(Continued)

*Primary Examiner* — Etsub Berhanu
(74) *Attorney, Agent, or Firm* — Renner, Otto, Boisselle & Sklar, LLP

(57) ABSTRACT

In an electroencephalogram recording apparatus: a classification section classifies a collected sound into one of categories concerning sound pressure; an accumulation determination section determines whether or not to record an electroencephalogram of a user based on whether a number of times of data accumulation has reached a target value for the category into which the sound is classified; and an accumulation section accumulates an electroencephalogram data and a sound data in association if the electroencephalogram data is determined to be recorded. A first value is designated as a target value for a first category into which sounds of an expected minimum value are classified. A second value is designated as a target value for a second category into which any sound having a sound pressure greater than the minimum value is classified. The accumulation determination section sets the first value to be equal to or greater than the second value.

17 Claims, 16 Drawing Sheets

(51) Int. Cl.
   *H04R 29/00* (2006.01)
   *A61B 5/0484* (2006.01)
   *A61B 5/12* (2006.01)
   *A61B 5/0482* (2006.01)

(52) U.S. Cl.
   CPC ........ *H04R 25/70* (2013.01); *A61B 2560/0247* (2013.01); *H04R 2225/39* (2013.01); *H04R 2225/41* (2013.01); *H04R 2225/43* (2013.01)

(56) References Cited

U.S. PATENT DOCUMENTS

| | | |
|---|---|---|
| 2002/0191804 A1* | 12/2002 | Luo et al. ............... 381/312 |
| 2003/0112987 A1* | 6/2003 | Nordqvist et al. .......... 381/312 |
| 2004/0064066 A1 | 4/2004 | John et al. |
| 2004/0204659 A1 | 10/2004 | John et al. |
| 2008/0260190 A1 | 10/2008 | Kidmose |
| 2009/0028351 A1 | 1/2009 | Andersen |
| 2010/0086143 A1 | 4/2010 | Norgaard et al. |
| 2010/0196861 A1 | 8/2010 | Lunner |
| 2010/0232633 A1 | 9/2010 | Nielsen |
| 2011/0152708 A1 | 6/2011 | Adachi et al. |
| 2011/0188664 A1 | 8/2011 | Morikawa et al. |

FOREIGN PATENT DOCUMENTS

| | | |
|---|---|---|
| JP | 2009-512376 T | 3/2009 |
| JP | 2010-004432 A | 1/2010 |
| JP | 2010-525696 T | 7/2010 |
| WO | 01/87147 A2 | 11/2001 |
| WO | 2007/112737 A1 | 10/2007 |
| WO | 2009/068028 A1 | 6/2009 |
| WO | 2011/001694 A1 | 1/2011 |
| WO | WO 2011/006681 A1 | 1/2011 |

OTHER PUBLICATIONS

"Jishoukanrendeni (ERP) Manyuaru-P300 WO Chushinni-(or "Event-Related Potential (ERP) Manual—mainly concerning P300-")", edited by Kimitaka Kaga et al., Shinohara Shuppan Shinsha, 1995, table 1 on p. 30 and partial English translation.
Chinese Search report for corresponding Chinese application No. 201280004219.8 (and English translation) dated Aug. 7, 2015.

* cited by examiner

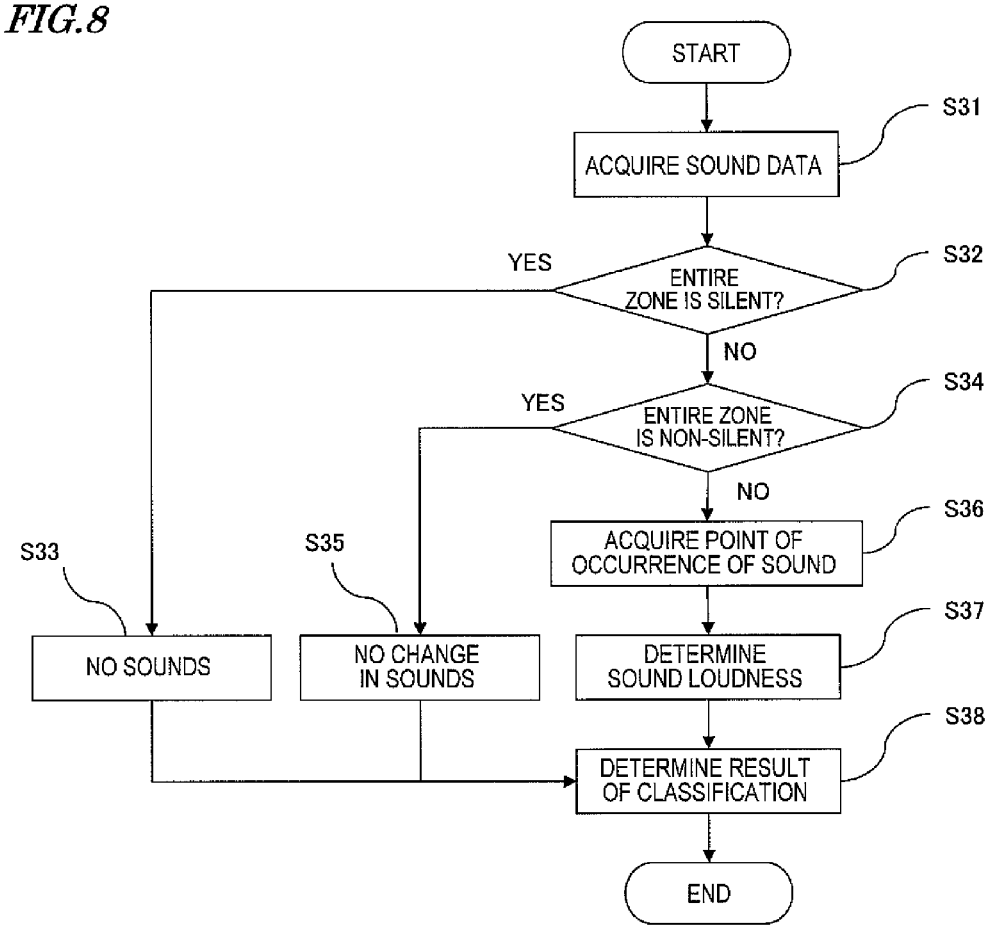

| RESULT OF SOUND CLASSIFICATION (CATEGORY) | TARGET NUMBER OF TIMES OF ACCUMULATION | CURRENT NUMBER OF ACCUMULATIONS |
|---|---|---|
| 0dB | 20 TIMES | 20 TIMES |
| 10dB | 20 TIMES | 15 TIMES |
| 20dB | 40 TIMES | 15 TIMES |
| 30dB | 40 TIMES | 20 TIMES |
| ... | ... | ... |
| 80dB | 10 TIMES | 10 TIMES |

ELECTROENCEPHALOGRAM RECORDING APPARATUS, HEARING AID, ELECTROENCEPHALOGRAM RECORDING METHOD, AND PROGRAM THEREOF

This is a continuation of International Application No. PCT/JP2012/000308, with an international filing date of Jan. 19, 2012, which claims priority of Japanese Patent Application No. 2011-026974, filed on Feb. 10, 2011, the contents of which are hereby incorporated by reference.

BACKGROUND

1. Technical Field

The present application relates to a technique of recording data to be used for the adjustment of a hearing aid. More specifically, the present application relates to an apparatus, method, and program for recording, together with sounds which a user may hear in various acoustic environments in daily life, electroencephalogram data which reflects states of hearing with respect to such sounds.

2. Description of the Related Art

In recent years, due to the aging society, increased opportunities for listening to loud music for long hours, and other influences, there is an increasing number of people suffering from presbycusis or hypacusia associated with acoustic traumas. Moreover, due to the downsizing and improved performance of hearing aids, users feel less of a psychological barrier against wearing hearing aids, and there is an increasing number of users who use hearing aids for the purpose of improving aural comprehension of daily conversations.

A hearing aid is a device for compensating for the deteriorated hearing ability of a user by increasing the amplitude of signals of specific frequencies, among various frequencies that compose sounds that are difficult for the user to hear. The amount of sound amplification which a user desires in a hearing aid varies depending on the level of deterioration in the hearing ability of the user, and also on the frequency band. Therefore, before beginning use of a hearing aid, a "fitting" is required for adjusting the amount of sound amplification for each frequency, in accordance with the hearing ability of each user.

Fitting is performed in order to ensure that the output sound pressure (i.e. fluctuations in air pressure that are perceivable as a sound) of each frequency from a hearing aid is at an MCL (most comfortable level: a sound pressure that is felt comfortable to a user).

In a first step of fitting, an audiogram is measured. An "audiogram" is a result of hearing assessment with respect to pure tones of different frequencies, performed at a hearing aid shop or hospital first, i.e., a result of assessing a hearing threshold value defining a smallest sound pressure of a pure tone that allows it to be heard. For example, an "audiogram" may be in the form of a diagram in which, for each of a number of sounds of different frequencies, the smallest sound pressure level (decibel value) that the user can aurally comprehend is plotted against frequency (e.g., 250 Hz, 500 Hz, 1000 Hz, 2000 Hz, 4000 Hz).

Then, from the audiogram, an initial adjustment is performed to determine an amount of amplification based on a fitting technique, which is a method of adjustment for providing amplification to a sound pressure level for attaining comfortable hearing. As necessary, a hearing aid shop further performs a speech sound intelligibility assessment, which involves presenting monosyllabic audios one by one to the user orally or from a sound source such as a CD, and making assessments as to whether the speech sounds were actually aurally comprehended, and thus makes a fine adjustment for the hearing aid. Through repetitions of such assessments and hearing aid adjustments, a hearing aid is obtained which has characteristics suited to the hearing of the user.

However, there has been a problem in that satisfactory adjustments for a hearing aid may not necessarily be made even through such fully-attended adjustments, because such hearing aid assessments and adjustments are made in a hearing aid shop and by a shop expert.

It is in the scenes of daily life that a user of a hearing aid actually wears the hearing aid, e.g., in the household, while watching television, or while going out. The optimum values of adjustment for the hearing aid will presumably differ from situation to situation. Conventionally, when any dissatisfaction with regard to the adjustment of a hearing aid is felt in the daily life, such scenes of dissatisfaction must be memorized, and conveyed to an expert. For example: there are no problems with conversations but television tends to sound too loud; while there are no problems conversing with an expert at the hearing aid shop, talking to the family still presents difficulties in hearing; and so on. As the hearing aid user conveys the dissatisfaction to the expert at the hearing aid shop, the expert makes a readjustment based on that result.

The difficulty in such adjustments is that the user needs to recall from memory those past experiences of difficulty of hearing, and try to explain the particular scene(s) and difficulty of hearing to the expert, who tries to estimate from the user's report what sort of difficulty of hearing was felt by the user in what sort of acoustic environment, and make a readjustment for the hearing aid. In the first place, subjective expressions of hearing may permit a lot of variations, and the difficulty of adjustments is further enhanced by reliance on memory.

This problem may be addressed by an approach of automatically recording the acoustic environments and states of hearing in scenes of daily life, this recorded data being acquired by an expert of a hearing aid shop either at the shopfront or via remote control, who analyzes the content of the data so that it is utilized as information for hearing aid fitting.

Conventional techniques related to this approach are as follows. Japanese National Phase PCT Laid-Open Publication No. 2009-512376 (hereinafter "Patent Document 1") discloses a hearing aid that has a data logger which logs the data of an input signal (ambient sound), and records results of characteristic analysis of parameters. This permits a quantitative understanding of what sort of acoustic environment(s) the user has been living in.

Japanese National Phase PCT Laid-Open Publication No. 2010-525696 (hereinafter "Patent Document 2") discloses a user-specific fitting method which, after an initial fitting is made, monitors and records a log of a history of choices made by a hearing aid user from among a set of plural gain parameters (i.e., a history of control operations made on the hearing aid), so that an expert at a hearing aid shop is able to determine from the log a final setting value for the hearing aid. This approach indirectly estimates the acoustic environment and state of hearing of the user by relying on the history information concerning which one of a set of plural gain parameters belonging to the hearing aid has been used most frequently.

Japanese Laid-Open Patent Publication No. 2010-4432 (hereinafter "Patent Document 3") discloses a hearing aid which, in response to each press of a store button by the user whenever feeling uncomfortable, records an ambient sound existing at that point in time, so that this stored sound is reproduced at the time of fitting for facilitating the fitting. Thus, the user is allowed to again hear at the hearing aid shop a sound which was difficult to aurally comprehend, etc., whereby the user is able to remember the scene which presented hearing difficulty. These techniques are all aimed at recording situations in scenes of daily life, with a view to realizing a more appropriate hearing aid fitting.

SUMMARY

The conventional technique needs further improvement in view of user's hearing.

One non-limiting and exemplary embodiment disclosed herein is directed to recording an ambient sound and information concerning the hearing of a user at each time, for the purpose of collecting an amount of data which is necessary for a fitting to be performed at a hearing aid shop, for example.

In one general aspect, an electroencephalogram recording apparatus according to the present disclosure comprises: an acoustic transducer configured to collect external sounds to generate sound data; an electroencephalogram measurement section configured to measure an electroencephalogram of a user to generate electroencephalogram data; a classification section configured to classify a sound collected by the acoustic transducer into one of a plurality of predetermined categories concerning a sound pressure of the sound; an accumulation determination section configured to determine whether or not to record the electroencephalogram data based on whether a number of times of data accumulation has reached a predetermined target value for the category into which the sound is classified; and an accumulation section configured to accumulate the electroencephalogram data and the sound data in association if the accumulation determination section determines that the electroencephalogram data is to be recorded, wherein, a target value is designated for each category; and among the plurality of categories, a first value is designated as a target value for a first category into which sounds of an expected minimum value are classified, and a second value is designated as a target value for a second category into which any sound having a sound pressure value greater than the minimum value is classified, the first value being set equal to or greater than the second value in the accumulation determination section.

According to the above aspect, it is possible to collect data which is needed for a fitting at a hearing aid shop in view of user's hearing.

These general and specific aspects may be implemented using a system, a method, and a computer program, and any combination of systems, methods, and computer programs.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

BRIEF DESCRIPTION OF THE DRAWINGS

FIG. 8 is a flowchart showing a procedure of processing by a classification section.

FIGS. 9A, 9B, and 9C are diagrams showing examples of sound classifications.

Figure 11B:
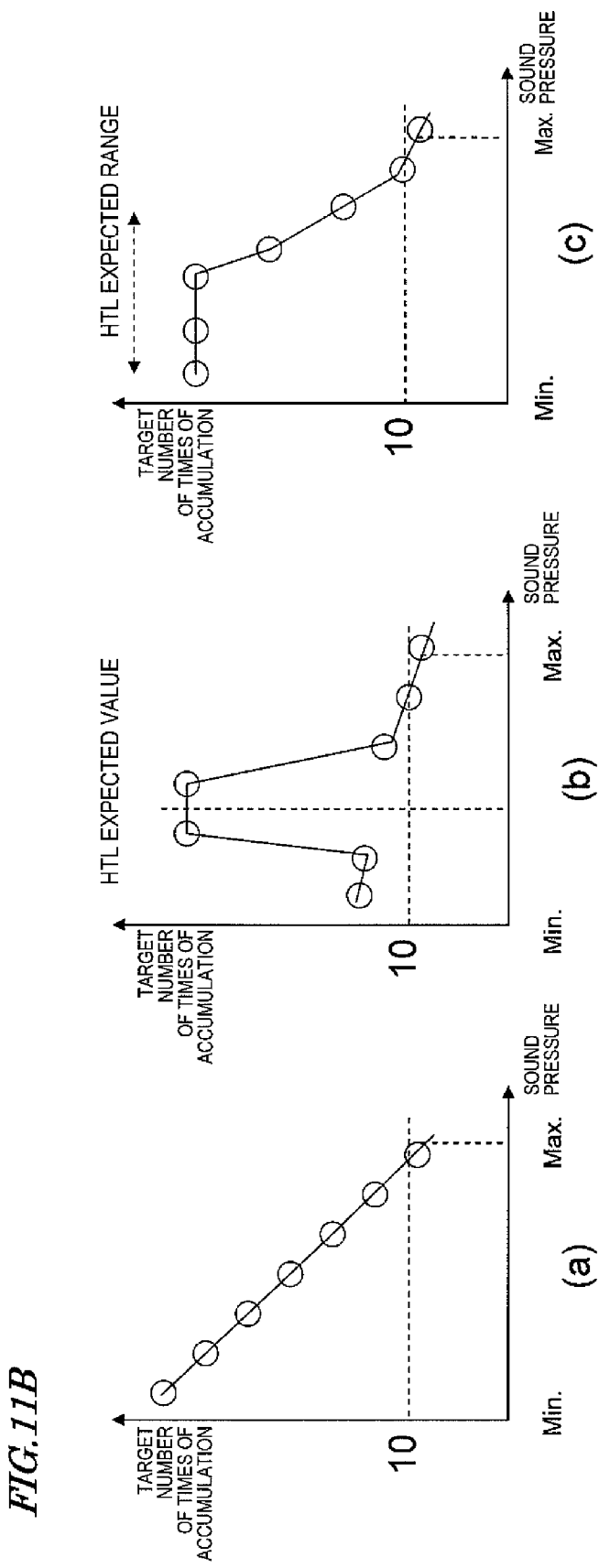

(a), (b), and (c) of FIG. 11B are diagrams showing relationships between a target number of times of accumulation and sound pressure.

Figure 12:
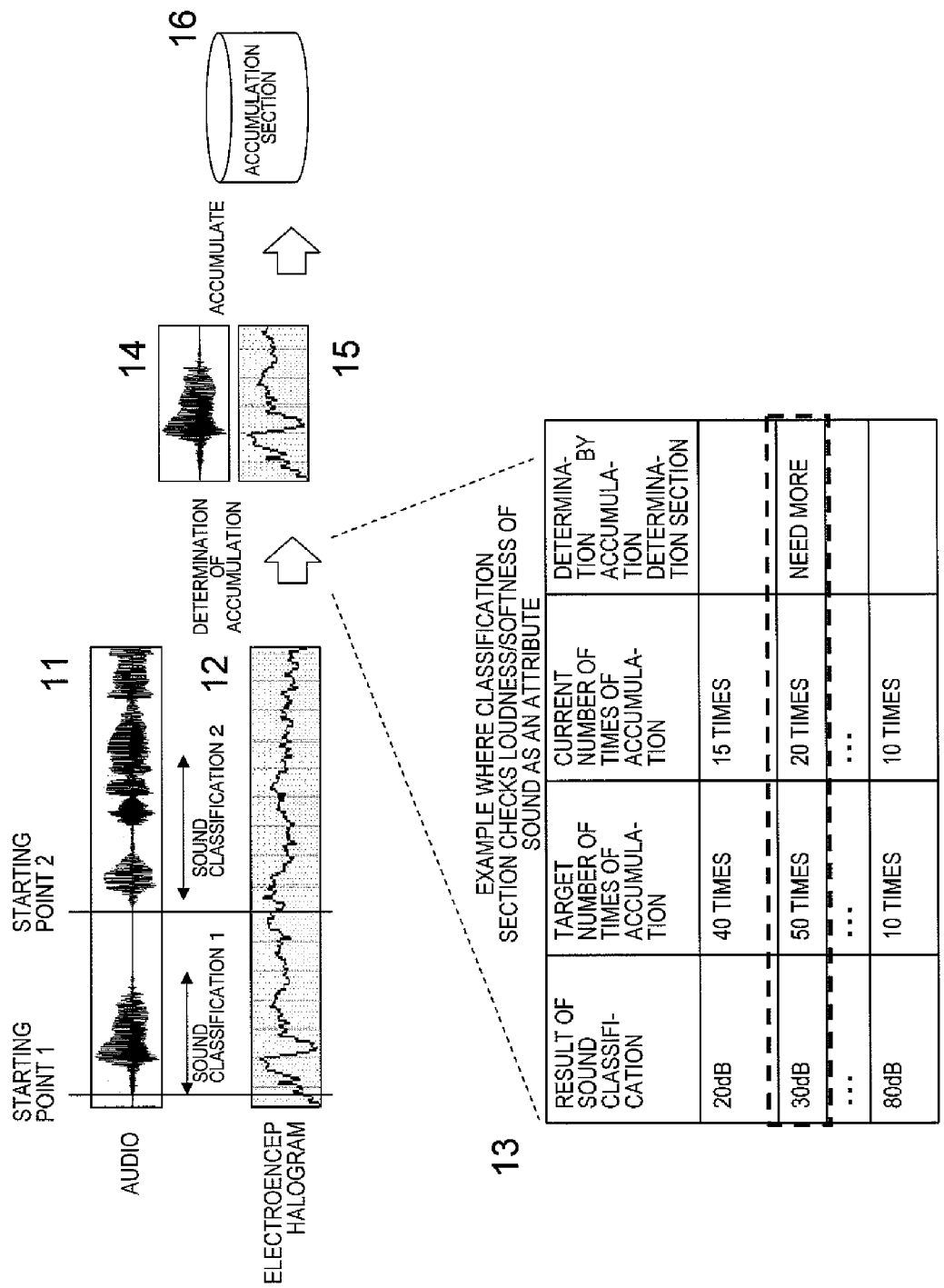

FIG. 12 is a diagram showing a processing instance of sound data and electroencephalogram data accumulation.

Figure 13A:
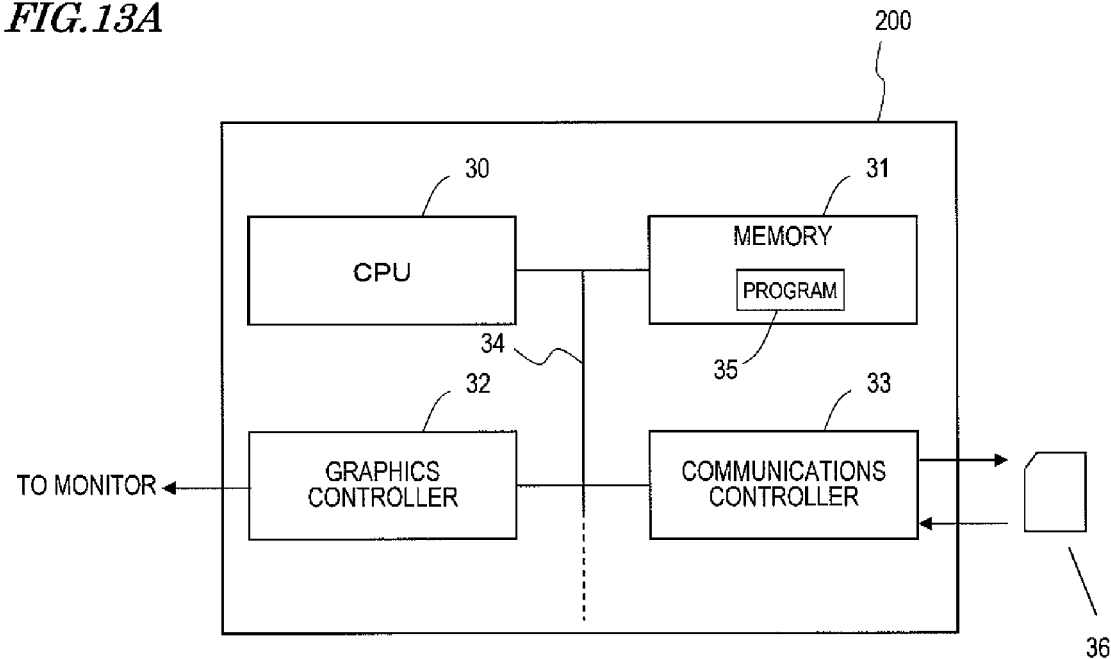

FIG. 13A is a diagram showing the hardware construction of a PC 200 which is installed at a hearing aid shop.

Figure 13B:
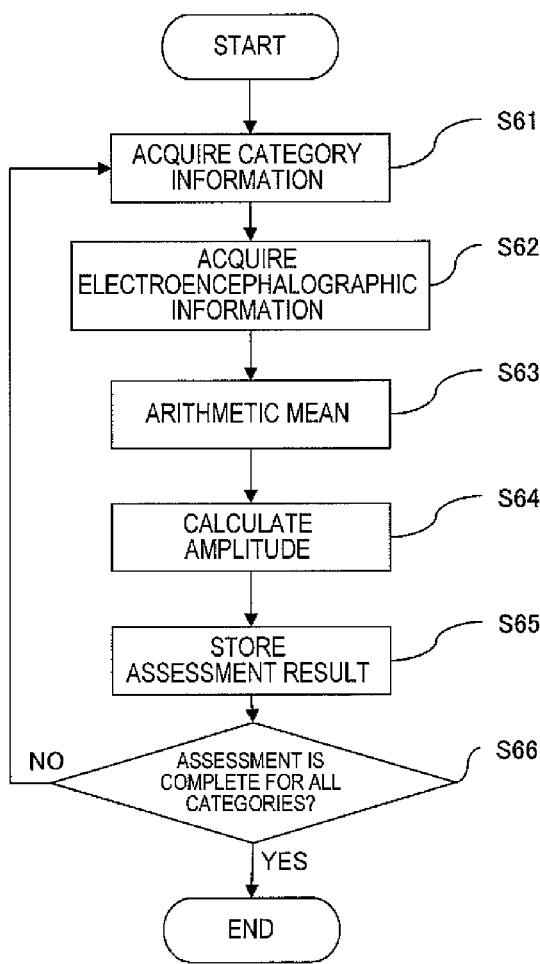

FIG. 13B is a flowchart showing a procedure of a process of performing hearing assessment based on accumulation results.

Figure 14:
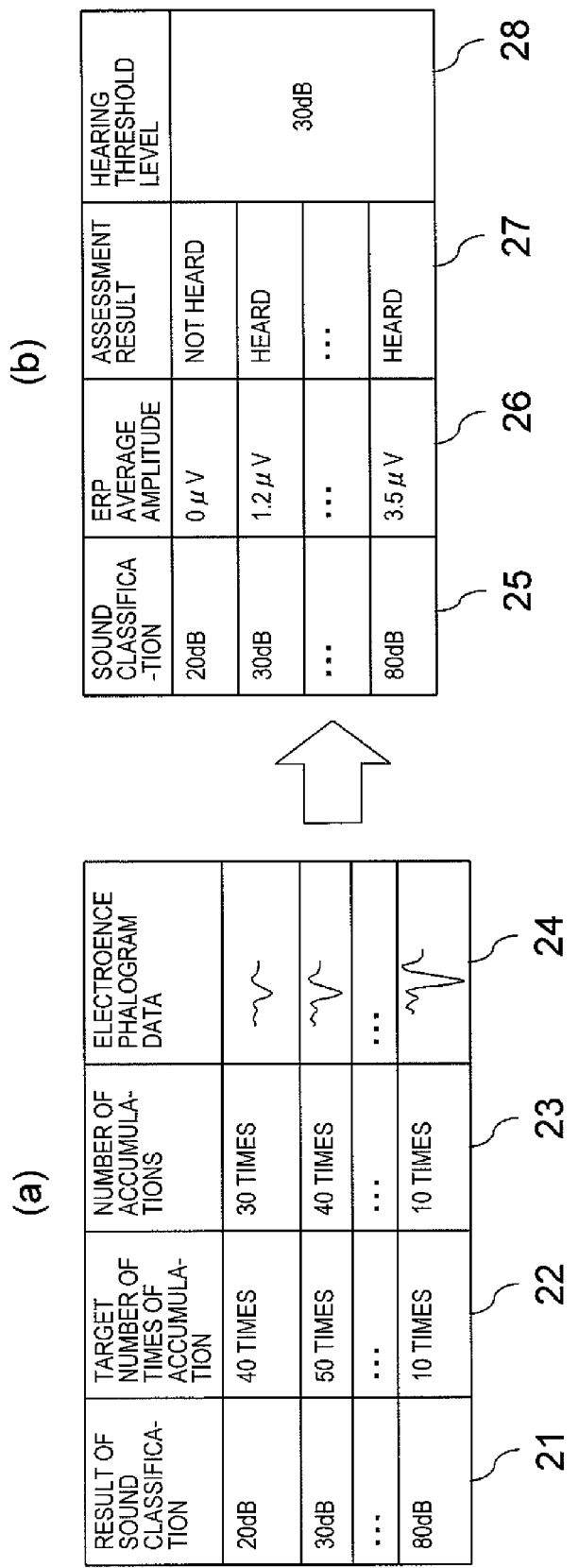

FIG. 14 is a diagram showing expected instances of conversion from accumulation results into assessment results.

Figure 15:
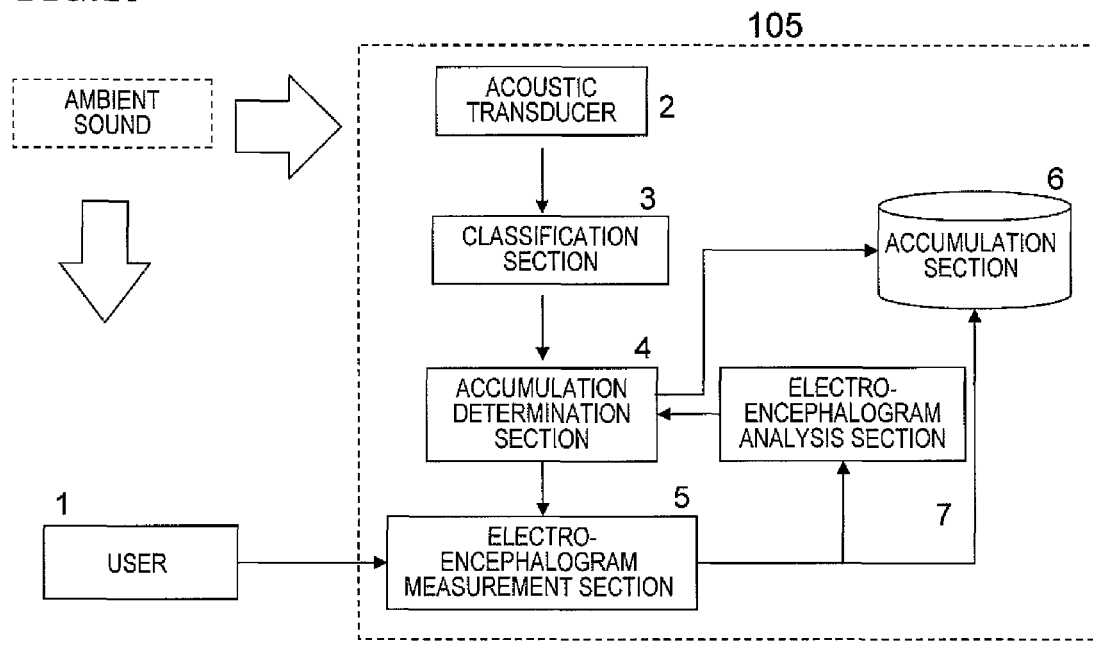

FIG. 15 is a diagram showing the construction of an electroencephalogram recording apparatus 105 according to Embodiment 2.

Figure 16:
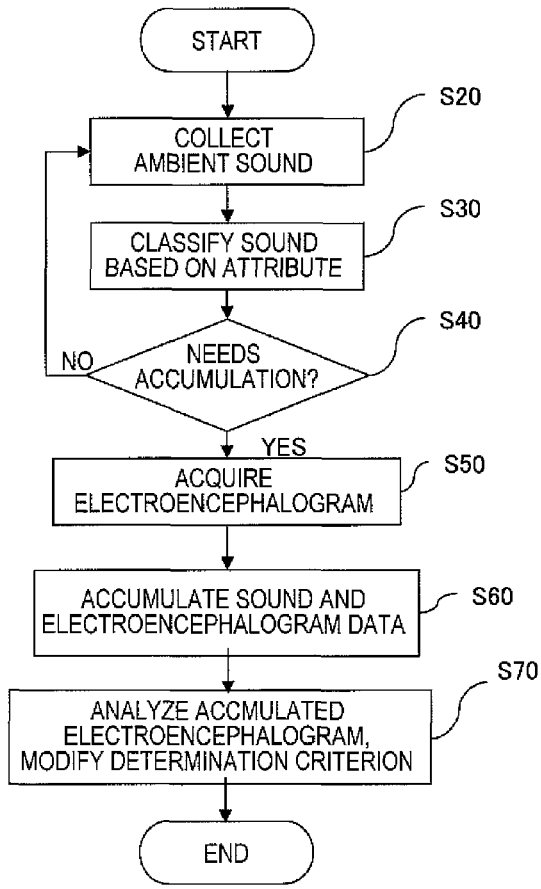

FIG. 16 is a flowchart showing a procedure by the electroencephalogram recording apparatus 105 according to Embodiment 2 in outline.

Figure 17:
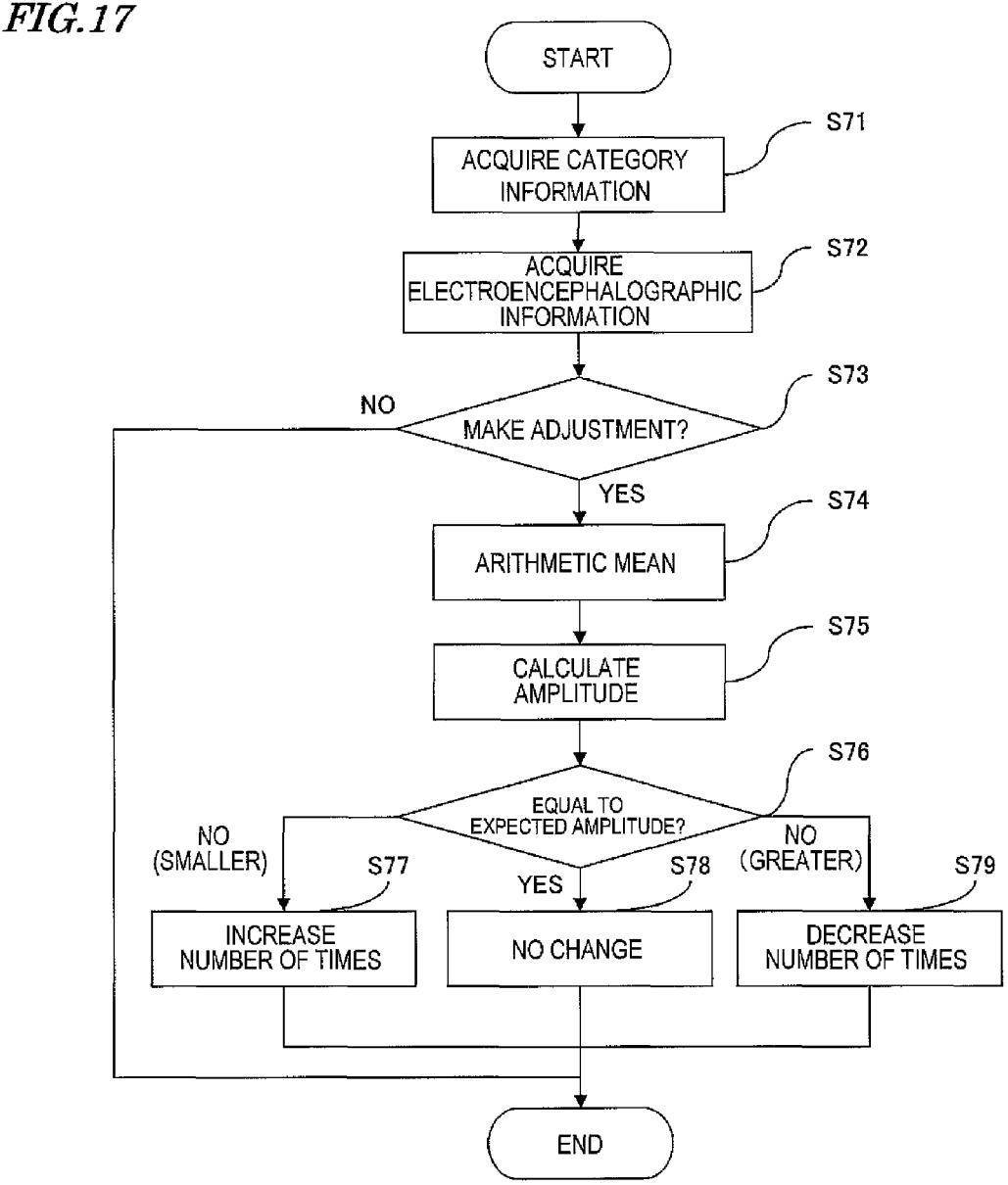

FIG. 17 is a flowchart showing a procedure of processing by an electroencephalogram analysis section.

Figure 18:
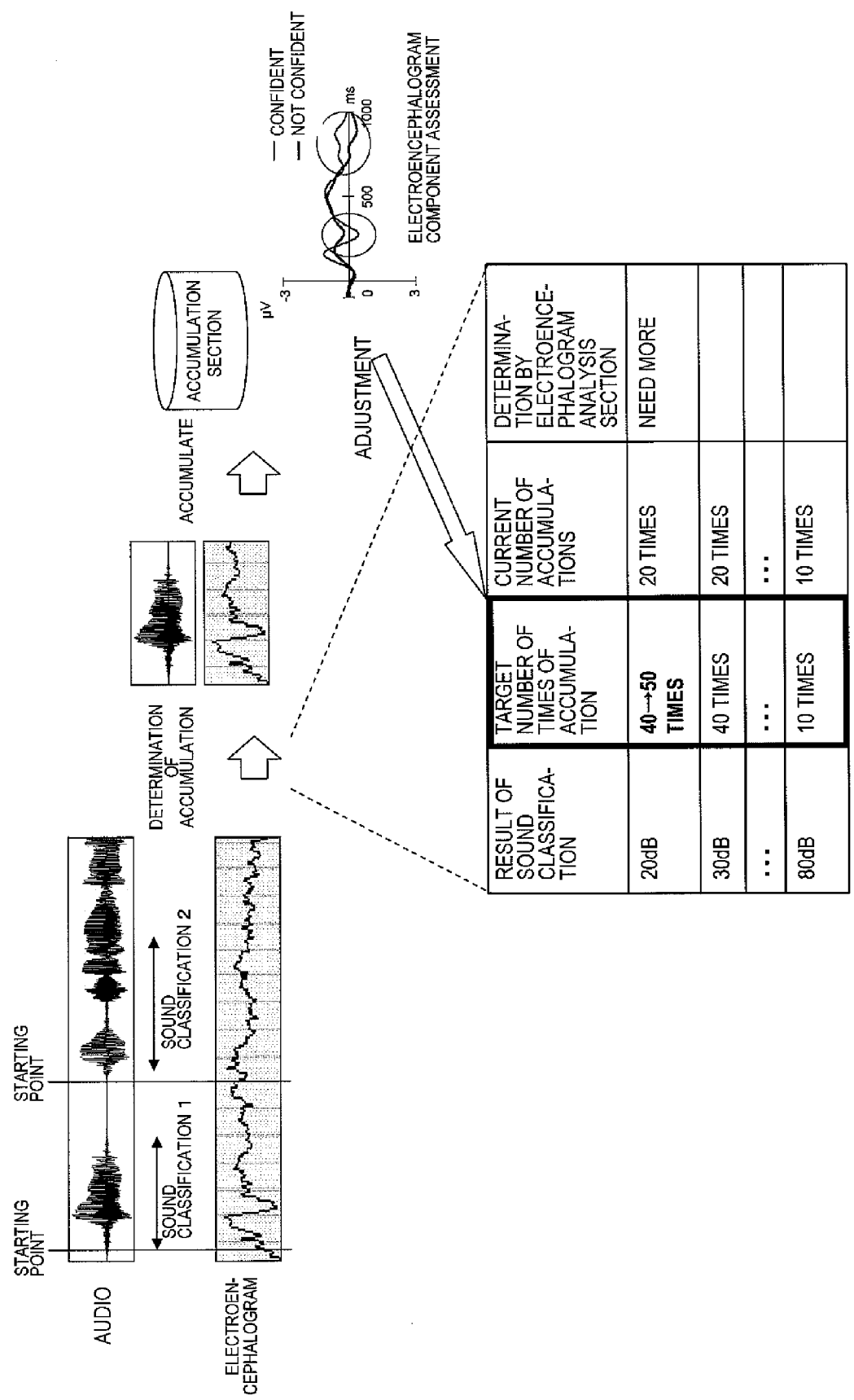

FIG. 18 is a diagram showing an exemplary process of modifying a determination criterion in accordance with the processing by an electroencephalogram analysis section 7.

Figure 19:
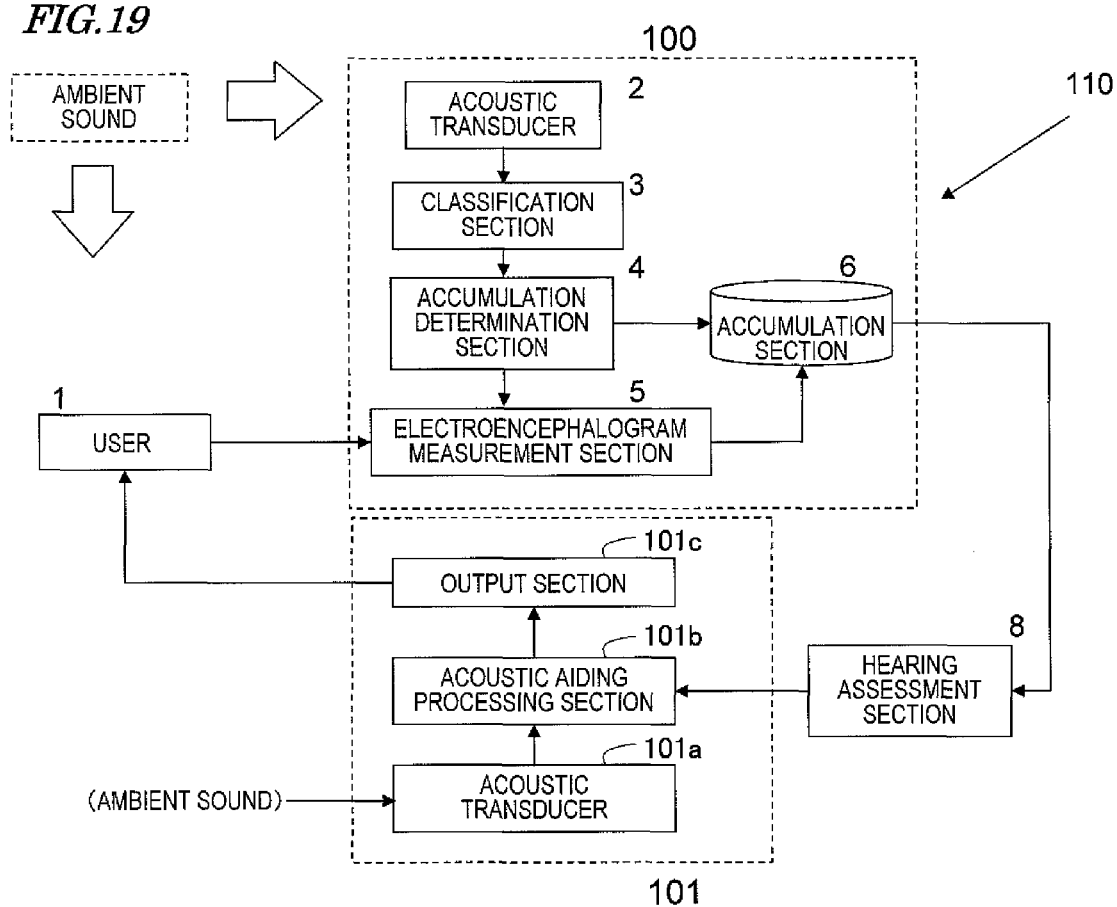

FIG. 19 is a diagram showing the construction of a hearing aid 110 according to an embodiment.

Figure 20:
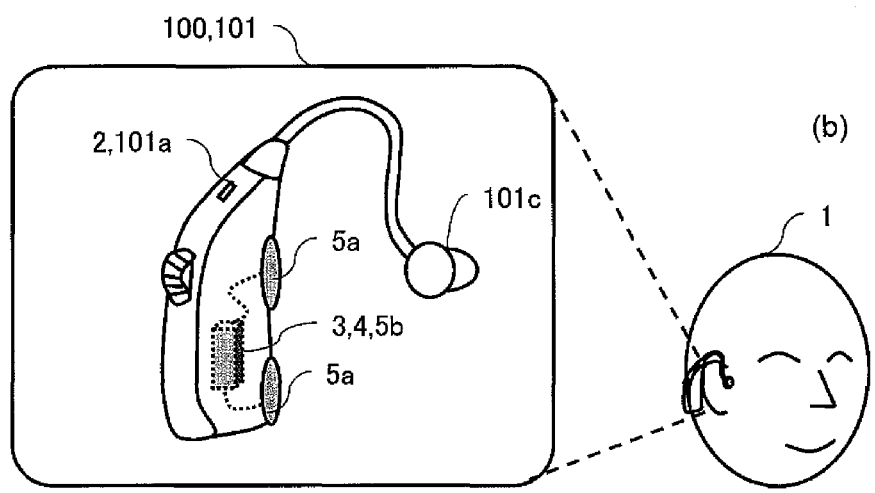

FIG. 20($a$) is a diagram showing an exemplary outer construction of a hearing aid 110 having an electroencephalogram recording apparatus 100 and a hearing aid section 101 which are integral with each other; FIG. 20($b$) is a diagram showing an example of wearing the hearing aid 110.

DETAILED DESCRIPTION

Before specific embodiments of the present disclosure are described, first of all, the problem of the conventional technique will be described.

While the conventional constitutions disclosed in Patent Document 1 and Patent Document 2 above make it possible to record sound information and record control operations for the hearing aid in scenes of daily life, they do not provide methods for recording how the user felt about the ambient sound at each time. Although the technique of Patent Document 3 indirectly records the intent of the user by the press of a button in each uncomfortable situation, it does not provide adequate recording of what sort of state of hearing existed. Each of these constitutions has a problem in that the most essential information, i.e., the user's hearing at each time is not recorded, and cannot be directly reproduced by merely looking at the log data at the hearing aid shop.

In one aspect of the present disclosure, an electroencephalogram recording apparatus comprises: an acoustic transducer configured to collect external sounds to generate sound data; an electroencephalogram measurement section configured to measure an electroencephalogram of a user to generate electroencephalogram data; a classification section configured to classify a sound collected by the acoustic transducer into one of a plurality of predetermined categories concerning a sound pressure of the sound; an accumulation determination section configured to determine whether or not to record the electroencephalogram data based on whether a number of times of data accumulation has reached a predetermined target value for the category into which the sound is classified; and an accumulation section configured to accumulate the electroencephalogram data and the sound data in association if the accumulation determination section determines that the electroencephalogram data is to be recorded, wherein, a target value is designated for each category; and among the plurality of categories, a first value is designated as a target value for a first category into which sounds of an expected minimum value are classified, and a second value is designated as a target value for a second category into which any sound having a sound pressure value greater than the minimum value is classified, the first value being set equal to or greater than the second value in the accumulation determination section.

The accumulation determination section may determine that the electroencephalogram data is to be recorded when the number of times of data accumulation in the category into which the sound is classified is smaller than the predetermined target value; and the accumulation determination section may determine that the electroencephalogram data is not to be recorded when the number of times of data accumulation in the category into which the sound is classified is equal to or greater than the predetermined target value.

When the accumulation determination section determines that the electroencephalogram data is to be recorded, the accumulation section may accumulate the sound and an electroencephalogram measured at a point in time at which the sound is collected, the sound and an electroencephalogram being kept in association.

The accumulation determination section may refer to the electroencephalogram or electroencephalograms and the sound or sounds accumulated in the accumulation section, and determine whether the electroencephalogram data is to be recorded or not based on whether the number of times of data accumulation in the category into which the sound is classified has reached the predetermined target value.

When an electroencephalogram component of interest in the electroencephalogram changes with the sound pressure value, the accumulation determination section may vary the target value in accordance with a level of the sound pressure value.

The accumulation determination section may designate an increasingly larger target value for a category into which sounds of increasingly smaller sound pressure values are classified.

The accumulation determination section may designate an increasingly smaller target value for a category into which sounds of increasingly larger sound pressure values are classified.

The accumulation determination section may designate an increasingly and linearly smaller target value for a category into which sounds of increasingly larger sound pressure values are classified.

The accumulation determination section may designate the first value as a common target value for two or more adjacent categories including the first category.

The electroencephalogram recording apparatus may further comprise an electroencephalogram analysis section configured to analyze the electroencephalogram or electroencephalograms accumulated in the accumulation section to determine whether the user has heard the sound or not, wherein, the accumulation determination section may increase the target value for a category corresponding to any sound determined by the electroencephalogram analysis section as not being heard by the user.

The electroencephalogram analysis section may analyze an electroencephalogram response from the data in the accumulation section to estimate an uncomfortableness threshold value at which the user has felt uncomfortable, and change the first value based on the uncomfortableness threshold value.

The classification section may classify the sound into one of a plurality of predetermined categories concerning a sound pressure and a frequency of the sound; and the electroencephalogram analysis section may identify a frequency which is difficult for the user to hear, and increases the target value for a category corresponding to the frequency.

The accumulation section may accumulate category information as a result of classification of the sound data, and accumulate an arithmetic mean of the electroencephalogram data for each category.

The electroencephalogram measurement section may measure the electroencephalogram by using a reference electrode and a ground electrode, at least one of the reference electrode and a ground electrode being placed in an ear.

In another aspect of the present disclosure, an electroencephalogram recording apparatus comprises: an acoustic transducer configured to collect external sounds; an electroencephalogram measurement section configured to measure an electroencephalogram of a user; a classification section configured to classify a sound collected by the acoustic transducer into one of a plurality of predetermined categories based on a sound pressure of the sound; an accumulation determination section configured to determine whether or not to record the electroencephalogram measured by the electroencephalogram measurement section based on whether a number of times of data accumulation has reached a predetermined target value for the category into which the sound is classified; and an accumulation section configured to accumulate in association the electroencephalogram and the sound for each category if the accumulation determination section determines that the electroencephalogram is to be recorded, wherein, a target value is designated for each of the plurality of categories; and an increasingly larger target value is designated for a category of an increasingly smaller sound pressure.

In another aspect of the present disclosure, a hearing aid comprises: any of the above electroencephalogram recording apparatuses; a hearing assessment section configured to perform a hearing assessment from data accumulated in the accumulation section; an acoustic aiding processing section configured to perform a different acoustic aiding process depending on an output result from the hearing assessment section; and an output section configured to present a result of the acoustic aiding process to the user in the form of a sound.

In another aspect of the present disclosure, an electroencephalogram recording method according to the present disclosure comprises the steps of: collecting external sounds to generate sound data; measuring an electroencephalogram of a user to generate electroencephalogram data; classifying a sound collected by the step of collecting external sounds into one of a plurality of predetermined categories concerning a sound pressure of the sound; determining whether the electroencephalogram data is to be recorded or not based on whether a number of times of data accumulation has reached a predetermined target value for the category into which the sound is classified; and accumulating the electroencephalogram data and the sound data in association if the determining step determines that the electroencephalogram data is to be recorded, wherein, a target value is designated for each category; and among the plurality of categories, a first value is designated as a target value for a first category into which sounds of an expected minimum value are classified, and a second value is designated as a target value for a second category into which any sound having a sound pressure value greater than the minimum value is classified, the first value being set equal to or greater than the second value when executing the accumulating step.

In another aspect of the present disclosure, a computer program according to the present disclosure is a computer program to be executed by a computer mounted in an electroencephalogram recording apparatus, wherein the computer program causes the computer in the electroencephalogram recording apparatus to execute the steps of: generating sound data of collected external sounds; acquiring electroencephalogram data measured of a user; classifying a collected sound into one of a plurality of predetermined categories concerning a sound pressure of the sound; determining whether the electroencephalogram data is to be recorded or not based on whether a number of times of data accumulation has reached a predetermined target value for the category into which the sound is classified; and accumulating the electroencephalogram data and the sound data in association if the determining step determines that the electroencephalogram data is to be recorded, wherein, a target value is designated for each category; and among the plurality of categories, a first value is designated as a target value for a first category into which sounds of an expected minimum value are classified, and a second value is designated as a target value for a second category into which any sound having a sound pressure value greater than the minimum value is classified, the first value being set equal to or greater than the second value when executing the accumulating step.

With an electroencephalogram recording apparatus and the like according to the present disclosure, ambient sounds in daily life and electroencephalogram data are recorded in sets, and only necessary amounts of ambient sounds and electroencephalogram data are accumulated for each attribute category of ambient sounds that are used for an electroencephalogram-based hearing assessment or the like. As a result, even with a small storage capacity, it is possible to collect data which is needed for a fitting at a hearing aid shop.

Hereinafter, by referring to the attached drawings, an electroencephalogram recording apparatus and method according to the present disclosure, as well as a computer program for operating such an electroencephalogram recording apparatus, will be described with respect to their respective embodiments.

According to embodiments of the present disclosure, when performing a hearing assessment, not only a sound occurring at the time of the assessment is utilized, but also an electroencephalographic response which reflects the loudness, ease of hearing, and the like of that sound are utilized. One technological characteristic of an electroencephalogram recording apparatus according to the present disclosure is that data of such sounds and electroencephalogram data are selectively accumulated. This provides an advantage of being able to collect data which is needed for the hearing assessment even when there is less than sufficient storage capacity, or, for the same storage capacity, collecting more data which is needed the hearing assessment.

Prior to the description of the embodiments, a method of hearing assessment based on electroencephalogram data will be described, along with an explanation as to why the required data amount differs depending on the electroencephalogram data.

In order to overcome the aforementioned problem of inability to record how a user felt about an ambient sound and what sort of hearing existed in an uncomfortable situation, the inventors first thought of an approach of recording an electroencephalographic response to each ambient sound. By analyzing an electroencephalographic response to a sound, it becomes possible to make an assessment as to the loudness of the sound, an assessment as to whether the speech sound was aurally distinguished or not, and so on, without requiring the user to orally answer on the hearing. By together recording such electroencephalogram data and sound data, it becomes possible to consecutively collect the states of hearing of the user concerning various sound stimulations at their respective points in time. Since this allows an expert at a hearing aid shop to know what state of hearing existed for which sound, the expert is able to set parameters more easily and accurately.

However, incessantly recording electroencephalogram data as well as ambient sound data in this manner will result in the recorded data volume being doubled, which is not preferable in terms of storable capacity and power consumption. In actual practice, it is foreseeable that these factors may present cost difficulties in maintaining operation for extended periods of time. Therefore, measures need to be taken to reduce the volume of data to be recorded.

Having recognized the problem associated with the additional use of electroencephalogram data, the inventors found that: in selectively recording a necessary amount of electroencephalogram data for the sound stimulation of interest, sound stimulations may be classified on the basis of an attribute which is suitable for electroencephalogram assessment, whereby control of data accumulation amounts can be made so that only necessary amounts of ambient sound and electroencephalogram data are accumulated. This will be specifically described below.

It is known that, when a user hears a sound, an electroencephalographic response that reflects the loudness, ease of hearing, and the like of the sound is evoked in the user. Such an electroencephalographic response, referred to as an event-related potential, can be quantitatively observed as a potential change in the electroencephalogram. Strictly speaking, an "event-related potential" means a transient potential fluctuation in the brain which occurs in temporal relationship with an external or internal event.

For example, concerning loudness/softness of sounds, it is known that an a characteristic waveform called an N1 component appears in the neighborhood of 100 milliseconds from the point of occurrence of a given sound as a starting point. As used herein, an "N1 component" refers to a potential waveform component having a negative peak (local maximum) that appears in the neighborhood of 100 milliseconds after hearing a sound. Generally speaking, "negative" means the event-related potential being smaller than 0 μV.

In the present specification, in order to define a component of an event-related potential, a point in time after the lapse of a predetermined time since a given point is expressed by referring to "about 100 ms", "in the neighborhood of 100 ms", "near 100 ms", etc., for example. This means possible inclusion of a range around the specific point of 200 ms in time. Generally speaking, there are 30 to 50 ms of differences (shifts) in event-related potential waveform between individuals, according to table 1 on p. 30 of "JISHOUKANRENDENI (ERP) MANYUARU—P300 WO CHUSHINNI— (or "Event-Related Potential (ERP) Manual—mainly concerning P300—"), edited by Kimitaka KAGA et al., Shinohara Shuppan Shinsha, 1995)". Therefore, the terms "about X ms" and "near X ms" mean that a breadth of 30 to 50 ms may exist before or after X ms (e.g., 100 ms±30 ms, 100 ms±50 ms, 200 ms±50 ms).

Figure 1:
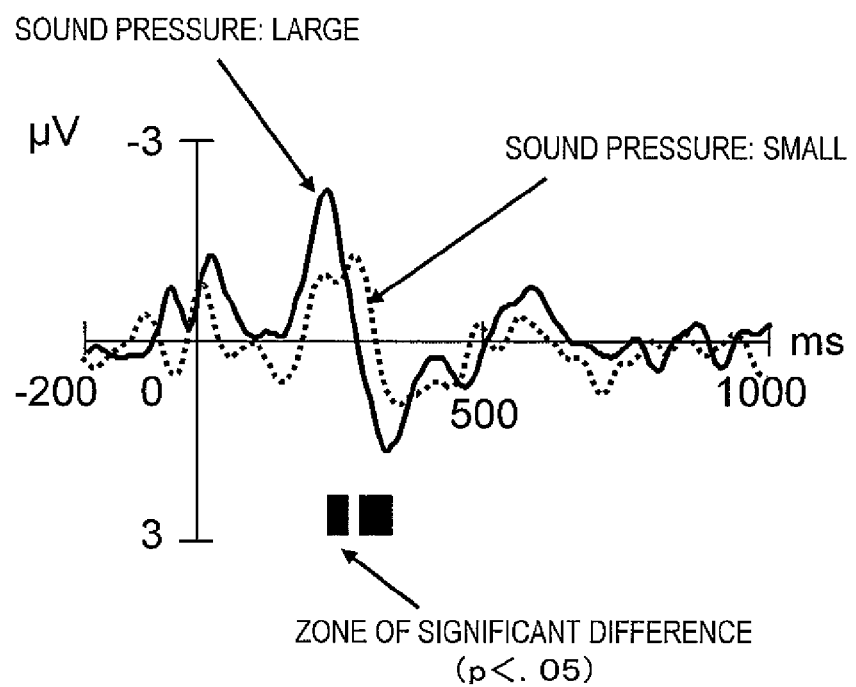
FIG. 1 is a diagram showing exemplary results of an experiment conducted by the inventors.

FIG. 1 shows exemplary results of an experiment conducted by the inventors. In FIG. 1, the horizontal axis represents time (in units of milliseconds), and the vertical axis represents the event-related potential waveform (in units of μV). Minus values are indicated in the upper direction on the vertical axis, whereas plus values are indicated in the lower direction.

It can be seen from FIG. 1 that the N1 component varies with the loudness of the sound (sound pressure). Specifically, it can be said that the N1 amplitude is large when a loud speech sound is heard (solid line), and small when a soft speech sound is heard (dotted line). Since the loudness of a sound that is felt as loud or soft depends on each user, checking the level of this component enables determination as to which particular sound was felt as loud or soft by the user. In this experiment, "loud sounds" had a sound pressure level of 60-65 dB, whereas "soft sounds" had a sound pressure level of 40-45 dB.

In FIG. 1, a negative peak appears in the neighborhood of 200 milliseconds, rather than in the neighborhood of 100 milliseconds. The reason is that this experiment measured a response where each speech sound (corresponding to one character of Japanese and being composed of a consonant and a vowel). It is known that a negative peak would appear in the neighborhood of 100 milliseconds when a pure tone such as a beep sound is presented. However, each audio presented in this experiment was a speech sound, spanning a certain duration in rising, so that the N1 component for the speech sound presumably had a corresponding delay, thus resulting in the neighborhood of 200 milliseconds.

Although a relationship between the level of the N1 component and sound pressure is discussed here, there may be other indices reflecting the level of sound pressure: the delaying nature of latency, i.e., the N1 component peak appearing at an increasingly later time (N1 latency) as the sound pressure decreases, and an N1–P2 amplitude difference, which can be obtained by using a P2 component (having a positive peak) after an N1 component is observed. Generally speaking, "positive" means the event-related potential being greater than 0 μV.

It must be noted that, when making this determination, a stable waveform may not be obtained through a single measurement because electroencephalogram data is affected by noises. This is because various disturbance components may be mixed in the electroencephalogram even when an electroencephalogram for a sound is to be assessed: e.g., a steadily occurring electroencephalogram component called the background electroencephalogram, and potential fluctuations which are linked with body motions and eye motions. Therefore, a method of taking an arithmetic mean of measured electroencephalogram components is adopted. By collecting plural instances of electroencephalographic responses to the same sound and calculating a mean of such electroencephalographic responses, it is ensured that steady components and noise components that are non-specific to the sound loudness cancel out one another, whereby only the necessary information will be obtained. The waveform of FIG. 1 has been obtained through such arithmetic means, and is indicative of characteristics of the electroencephalogram.

Figure 2C:
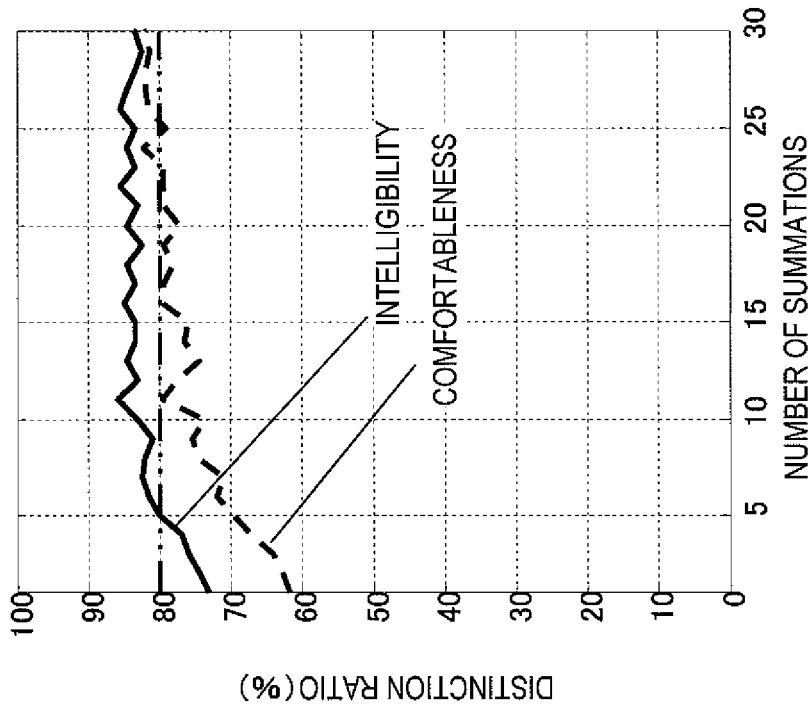
FIGS. 2A, 2B, and 2C are diagrams showing exemplary results of another experiment conducted by the inventors.
Figure 2A:
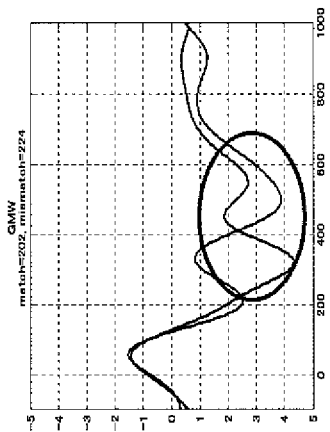
Figure 2B:
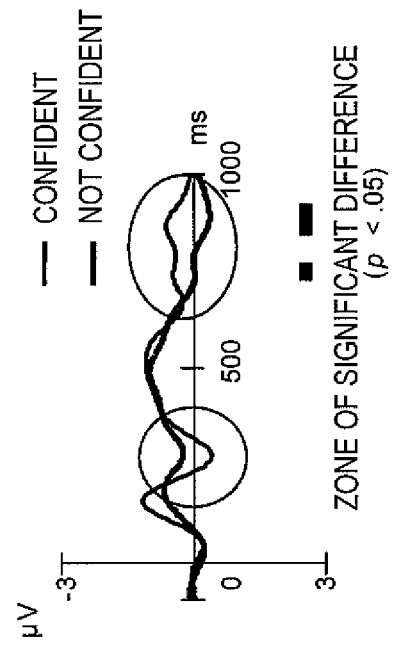

This number of summations will be further described. FIGS. 2A to 2C show exemplary results of another experiment conducted by the inventors. Each is directed to another instance of hearing characteristics assessment, based on an electroencephalogram component which is distinct from the N1 component. FIG. 2A illustrates a component which reflects whether a test subject thinks that a sound has been clearly aurally comprehended or not. A difference of about 4 μV was found between the respective electroencephalogram components indicative of whether the sound was felt clear or not in the intelligibility assessment. FIG. 2B illustrates a component which reflects how confidently a test subject believes that a sound has been accurately aurally comprehended. The fact that a test subject has accurately aurally comprehended a sound is presumably indicative that the sound has been comfortably heard. A difference of about 1 μV was found between the respective electroencephalogram components in the comfortableness assessment. In the present specification, the respective components shown in FIG. 2A and FIG. 2B will be referred to as "intelligibility" and "comfortableness".

FIG. 2C shows data resulting from studying necessary numbers of summations for conducting assessments. The horizontal axis represents the number of summations, and the vertical axis represents the distinction ratio. It will be seen that the distinction ratio increases as the number of summations increases. For example, assuming that the accuracy needed for distinction is 80%, the component associated with intelligibility assessment shown in FIG. 2A attains a necessary accuracy through about 5 summations, which is relatively few; on the other hand, the component associated with comfortableness assessment requires as many summations as 20 times or more. This is because the electroencephalogram component differs depending on the interest of assessment. In other words, whereas intelligibility creates a difference as large as about 4 μV as to being clear or not, comfortableness only creates a small difference of about 1 μV. This difference manifests itself as different steady electroencephalogram components or different SN ratios (signal level relative to noise), and hence different necessary numbers of summations.

Similarly, also in the case of the N1 component shown in FIG. 1, the responses to soft sounds have a small component, whereas the responses to loud sounds have a large component. FIG. 1 will now be discussed again from this standpoint. In FIG. 1, the louder sounds had a sound pressure level of 60-65 dB, and the soft sounds had a sound pressure level of 40-45 dB. The N1 component in this experiment, which is expressed in terms of a negative peak amplitude between 100 ms and 300 ms, was −2.19 μV under the large-sound pressure conditions, and −1.41 μV under the small-sound pressure conditions. The waveform for each sampling point was subjected to a t-test, which found significant difference in a zone from 218 ms to 238 ms and a zone from 272 ms to 332 ms (p<0.05). Thus, since the N1 component level also varies with sound pressure, the necessary number of summations will vary, too. Especially, the response near the hearing threshold level (HTL) is particularly small, so that a particularly large number of summations will be required to check for an N1 component response near that sound pressure.

Thus, it was found that an arithmetic mean needs to be performed in order to cope with the noise mixing into the electroencephalogram data. It was also indicated that, when there are limitations of recording capacity and power consumption in an electroencephalogram recording apparatus, only a necessary and sufficient amount of data should be accumulated, and the necessary and sufficient data amount needs to be adjusted according to the loudness of the ambient sound and the level of the electroencephalogram component to be assessed.

Hereinafter, embodiments of electroencephalogram recording apparatuses, which are obtained by giving consideration to such characteristics, will be described with reference to the drawings.

(Embodiment 1)

Figure 3:
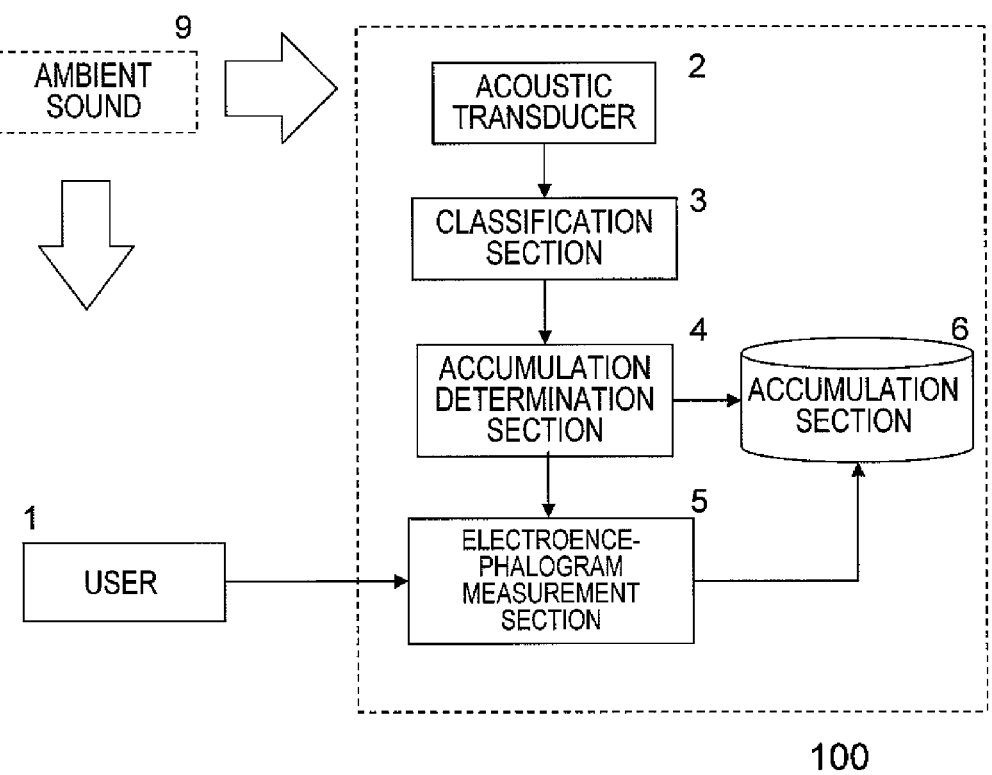
FIG. 3 is a diagram showing the construction of an electroencephalogram recording apparatus 100 according to Embodiment 1.

FIG. 3 shows the construction of an electroencephalogram recording apparatus 100. The electroencephalogram recording apparatus 100 records responses of an electroencephalogram of a user 1 to ambient sounds 9.

The electroencephalogram recording apparatus 100 includes an acoustic transducer 2, a classification section 3, an accumulation determination section 4, an electroencephalogram measurement section 5, and an accumulation section 6.

The acoustic transducer 2 includes a microphone and an audio input circuit, for example, as will be described later. The acoustic transducer 2 collects the ambient sounds and output them to the classification section 3. The acoustic transducer 2 may digitize the collected sounds through sampling and quantization, and output them as sound data, for example. For a sound quality equivalent to CDs, for example, the sound data may be 44.1 KHz, 16-bit data which is linear PCM-encoded. Note that the encoding method, the sampling frequency, the quantization bit rate, and the like may be changed in accordance with what the assessment is directed to.

The electroencephalogram measurement section 5 is an electroencephalograph, for example. The electroencephalogram measurement section 5 measures an electroencephalogram of the user 1. The electroencephalogram measurement section 5 outputs the resultant electroencephalogram signal as electroencephalogram data. The specific method of generating electroencephalogram data from the electroencephalogram signal may be arbitrarily chosen. For example, similarly to sounds, the electroencephalogram signal may be digitized through sampling and quantization.

Based on an attribute of the sound to be subjected to hearing assessment, the classification section 3 classifies the sound data having been output from the acoustic transducer 2 into a certain attribute category. The attributes of a sound may include the loudness (sound pressure) of the sound, the frequency of the sound, and so on. An example may be where an assessment is made to determine the loudness at which sounds in the surroundings are audible to the user 1, i.e., whether an electroencephalographic response is observed or not.

In accordance with the attribute category of the ambient sound, the accumulation determination section 4 determines whether the electroencephalogram data is to be accumulated or no. If the accumulation determination section 4 determines that the electroencephalogram data is to be accumulated, the accumulation section 6 accumulates the electroencephalogram data having been output from the electroencephalogram measurement section 5 and the sound data used for the determination.

The accumulation section 6 may be a recording mechanism having a flash memory card and a control circuit therefor, for example.

Although the present specification illustrates the acoustic transducer 2 as a component element of the electroencephalogram recording apparatus 100, such construction is exemplary. The acoustic transducer 2 is not an essential component element of the electroencephalogram recording apparatus 100. For example, it suffices if the classification section 3 of the electroencephalogram recording apparatus 100 is able to receive the ambient sounds 9 that have been collected. Moreover, the electroencephalogram measurement section 5 is not an essential component element of the electroencephalogram recording apparatus 100. For example, in the case where the electroencephalogram measurement section 5 is implemented as a separate electroencephalograph, the electroencephalogram recording apparatus 100 may simply be capable of receiving electroencephalogram data from that electroencephalograph.

Similarly, the accumulation section 6 is not an essential component element of the electroencephalogram recording apparatus 100, and may be a separate storage device (e.g., a hard disk drive or an optical disk drive on which an optical disk is mounted) that is provided external to the electroencephalogram recording apparatus 100 and connected wiredly or wirelessly to the electroencephalogram recording apparatus 100. Furthermore, the accumulation section 6 may be connected directly, or via a network, to the electroencephalogram recording apparatus 100. The electroencephalogram recording apparatus 100 may at least have the classification section 3 and the accumulation determination section 4.

Figure 4A:
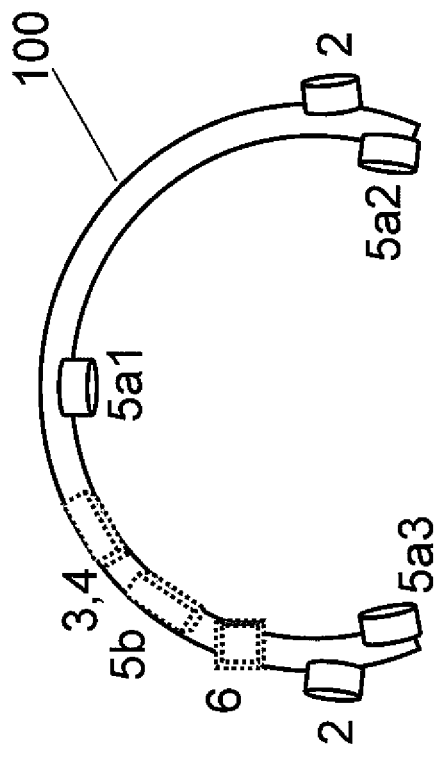
FIG. 4A is a diagram showing a specific implementation of the electroencephalogram recording apparatus 100.
Figure 4B:
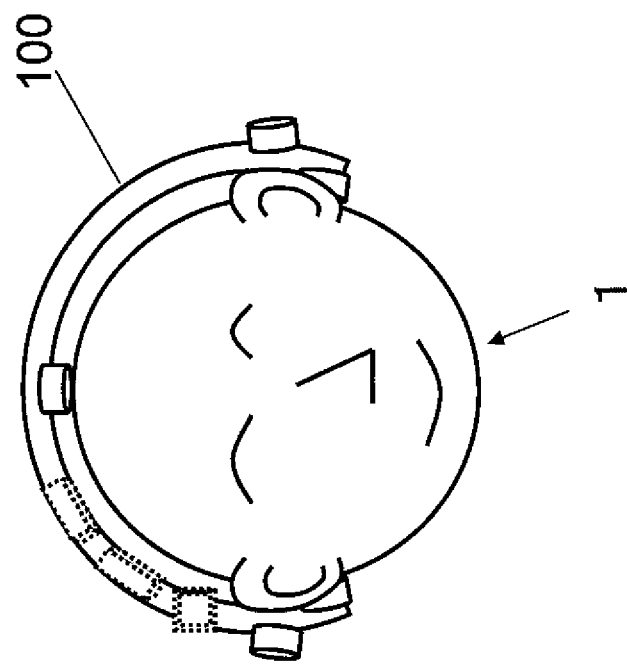
FIG. 4B is a diagram showing how the electroencephalogram recording apparatus 100 may be used when performing a hearing assessment prior to purchase of a hearing aid.

FIG. 4A shows a specific implementation of the electroencephalogram recording apparatus 100. FIG. 4B shows the electroencephalogram recording apparatus 100 being worn by the user 1. There may be two usages of the electroencephalogram recording apparatus 100: when it is worn to assess the hearing ability of the user 1 prior to purchasing a hearing aid or the like; and assessing, once a hearing aid has been purchased and subjected to an initial setup, how optimally the hearing aid is adjusted. FIG. 4B illustrates how the electroencephalogram recording apparatus 100 may be used when performing a hearing assessment prior to buying a hearing aid. Any component element in FIGS. 4A and 4B corresponding to a component element in FIG. 3 is denoted by the same reference numeral.

As shown in FIG. 4B, the user 1 wears the electroencephalogram recording apparatus 100 on his or her head. A headset-type electroencephalogram recording apparatus 100 is contemplated in this example.

One example of the electroencephalogram measurement section 5 may include electrodes 5a for electroencephalogram measurement and an electroencephalogram signal amplification section (biometric amplifier) 5b. In order to measure a potential change on the head in the form of an electroencephalogram, it is desirable that the electrodes are shaped so as to be capable of touching the head at a predetermined position. The predetermined position that are suitable for hearing assessment may change depending on the electroencephalogram component to be measured.

Figure 5:
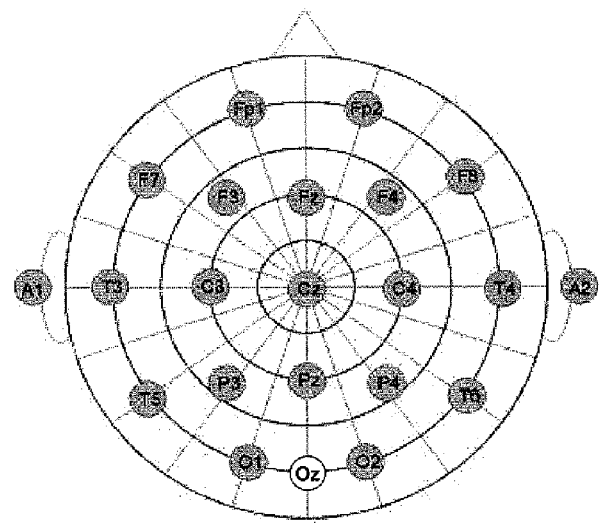
FIG. 5 is a diagram showing electrode positions according to the International 10-20 system (10-20 System).

FIG. 5 shows electrode positions according to the International 10-20 system (10-20 System). By using this position designation, for example, evoked responses to sounds can easily be recorded by placing a leading electrode at a position such as parietal Cz, C3, or C4. As for the other electrodes, for example, a reference electrode may be placed at A1, a ground electrode at A2, and so on. This will allow the electroencephalogram to be obtained. The aforementioned electrode positions are also used when measuring an electroencephalogram component (e.g., an N1 component) that is utilized in the present embodiment.

Other than the electrodes 5a, the electroencephalogram recording apparatus 100 includes a microphone(s) 2 corresponding to the acoustic transducer 2. Since it is necessary to collect sounds which are as close to the sounds heard by the user as possible, they are preferably placed at positions close to the ears. In the case where responses to sounds coming from the right or the left are to be individually assessed, it is preferable to provide respective microphones for the right ear and the left ear.

The classification section 3, the accumulation determination section 4, and the electroencephalogram measurement section 5 (biometric amplifier 5b) included in the electroencephalogram recording apparatus 100 are implemented as signal processing circuitry (electronic circuit), and is accommodated in a headset-type housing. Such signal processing circuitry is electrically connected to the microphones and electrodes (not shown). The accumulation section 6 is implemented as a storage medium such as a memory card. At a hearing aid shop, exchange of data occurs through handing of a memory card, or via communications.

Figure 6:
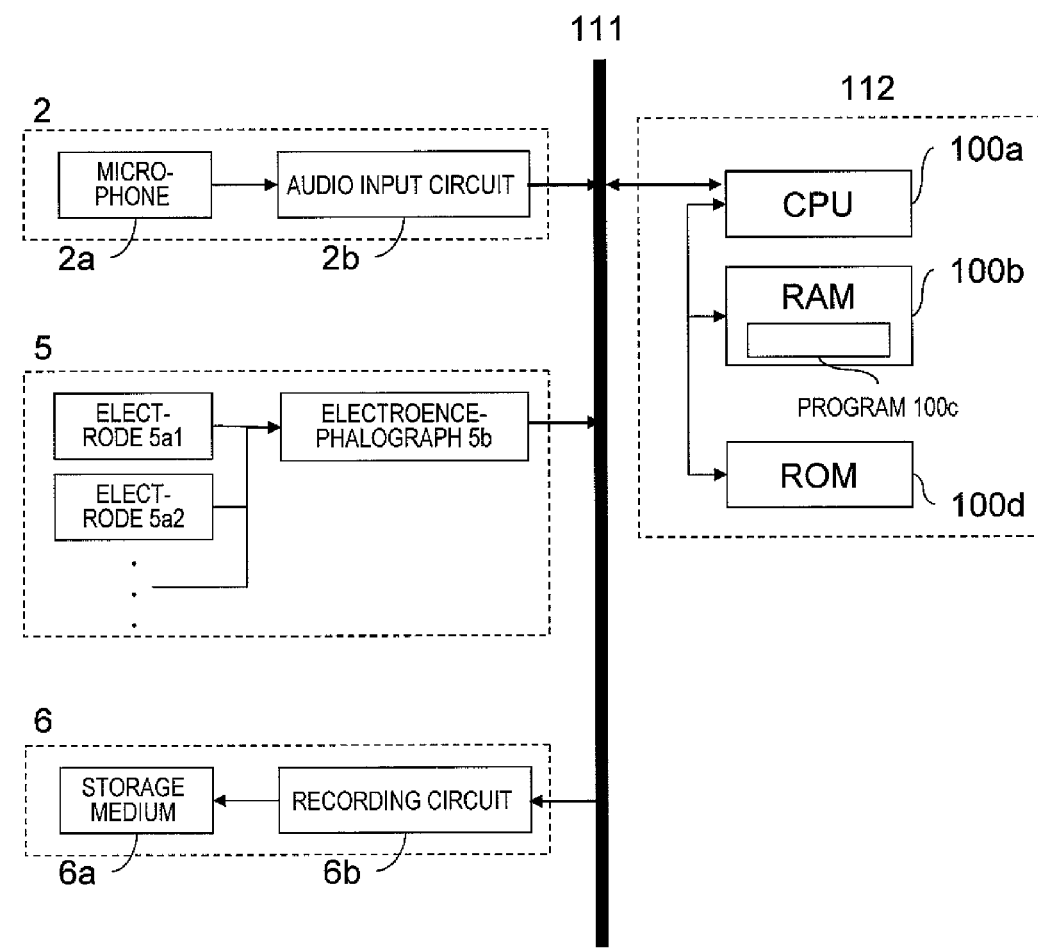
FIG. 6 is a diagram showing the hardware construction of the electroencephalogram recording apparatus 100 according to Embodiment 1.

FIG. 6 shows a hardware construction for the electroencephalogram recording apparatus 100 according to the present embodiment. The electroencephalogram recording apparatus 100 includes a CPU 100a, a RAM 100b, and a ROM 100d which implement a signal processing section 112 (i.e., the classification section 3 and the accumulation determination section 4) of the electroencephalogram recording apparatus 100, with a processing program 100c being stored in the RAM 100b.

As an input/output device with the exterior, a microphone 2a and an audio input circuit 2b are provided as the acoustic transducer 2. As the electroencephalogram measurement section 5, an electroencephalograph 5b and electrodes 5a1 and 5a2 are provided. Furthermore, a storage medium 6a and a recording circuit 6b are provided as the accumulation section 6.

These devices are interconnected via a bus 111 so that data exchange among them is possible. For example, executing the program 100c stored in the RAM 100b, the CPU 100a classifies the sound data which is output from the acoustic transducer 2 in accordance with the attribute category of the sound, and determines whether it is to be accumulated or not. Thereafter, as necessary, together with the electroencephalogram data which is output from the electroencephalogram measurement section 5, the CPU 100a records the sound data having been output from the acoustic transducer 2 to the storage medium in the accumulation section 6.

Note that the electroencephalogram recording apparatus 100 may be implemented by using a single-chipped CPU, RAM, and ROM, or implemented as a piece of hardware (e.g., a DSP) consisting of a semiconductor circuit having a computer program incorporated therein. Such a DSP can realize all functions of the aforementioned CPU, RAM, ROM, audio input/output circuitry, and the like on a single integrated circuit.

The aforementioned computer program 100c may be distributed on the market in the form of a product recorded on a storage medium such as a CD-ROM, or transmitted through telecommunication lines such as the Internet.

Next, processing by the electroencephalogram recording apparatus as such will be specifically described with reference to FIG. 7 to FIG. 14.

Figure 7:
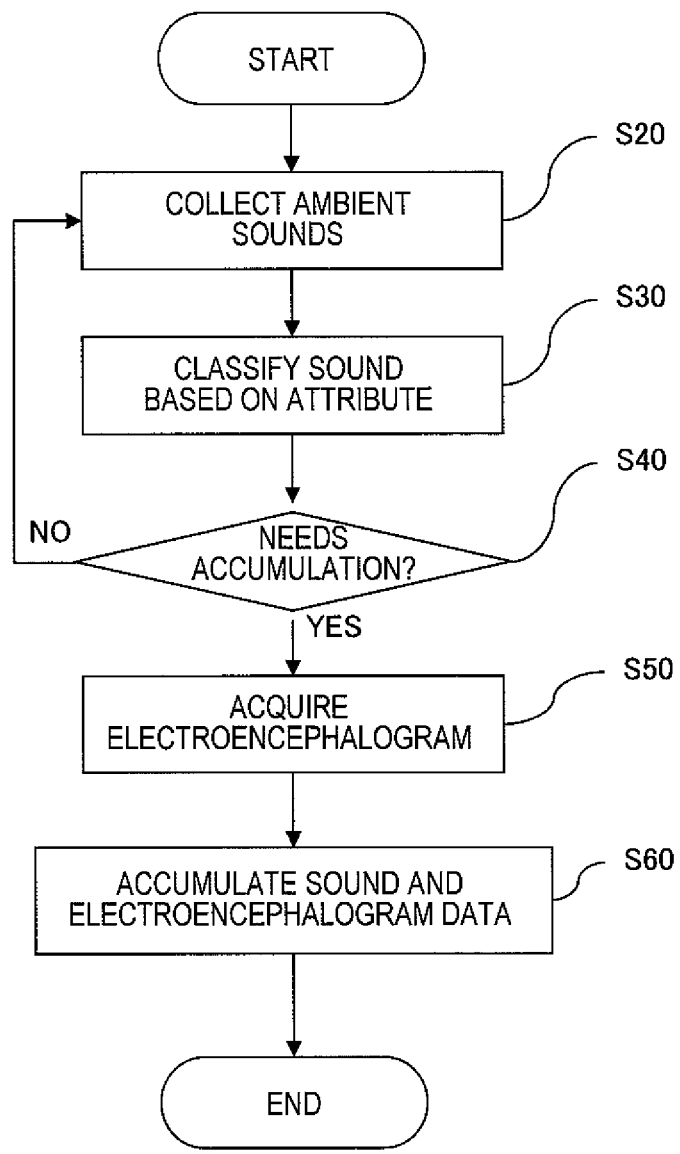
FIG. 7 is a flowchart showing a procedure of processing by the electroencephalogram recording apparatus 100 according to Embodiment 1 in outline.

FIG. 7 shows a combined procedure of processing by the electroencephalogram recording apparatus 100 according to the present embodiment in outline. Some of the steps of the processing shown in FIG. 7 will be described later with reference to a more detailed flowchart.

FIG. 7 shows a general processing procedure by the electroencephalogram recording apparatus 100.

First, at step S20, the acoustic transducer 2 collects the ambient sounds 9. The ambient sounds 9 are inclusive of all audio information that reaches the ears of the user, which may include conversational voices and the like.

At step S30, the classification section 3 analyzes the collected sound(s), and classifies it into one of a plurality of attribute categories. The attribute may be the loudness (sound pressure) of the sound(s) or the like, for example. The sound pressure is calculated from the loudness/softness of the collected sound data.

At step S40, the accumulation determination section 4 determines whether the current state requires accumulation of data. A state which requires accumulation means a state where the electroencephalogram data that has been evoked in response to sounds has not reached a necessary amount. If it is determined at step S40 that accumulation should not be performed, the process returns to step S20; if it is determined that accumulation should be performed, the process proceeds to step S50.

At step S50, the electroencephalogram measurement section 5 acquires electroencephalogram data. The electroencephalogram measurement section 5 is incessantly measuring an electroencephalogram. The previous process of step S40 has sent out information concerning a zone in which to cut out the electroencephalogram data, and based on this information, the electroencephalogram measurement section 5 acquires an event-related potential corresponding to the zone in which to cut out the electroencephalogram data. Presumably, the zone in which to acquire the event-related potential may be from −100 milliseconds to 600 milliseconds based on the point of occurrence of an ambient sound, for example. The zone from −100 milliseconds to 0 milliseconds will be used for baseline correction, whereas 0 milliseconds to 600 milliseconds will be regarded as a change in the event-related potential for the assessment. The zone in which to acquire the event-related potential varies depending on the electroencephalogram component to be assessed. For example, in the case where an N1 component near 100 milliseconds in response to an audio is the main interest, the event-related potential in a zone from −100 milliseconds to 300 milliseconds may be acquired.

Although the process of electroencephalogram data cutting is illustrated as being performed by the electroencephalogram measurement section 5, this is exemplary. In actuality, it is performed by the CPU 100a shown in FIG. 6. Since the CPU 100a also functions as the accumulation determination section 4, the accumulation determination section 4 might as well be regarded as performing the process of electroencephalogram data cutting.

At step S60, the accumulation section 6 accumulates the sound data, if it has been determined by the accumulation determination section 4 as needing accumulation, together with the electroencephalogram data, on the storage medium. Accumulating the sound data and the electroencephalogram data in association enables an assessment, back at the hearing aid shop, as to what state of hearing the user experienced for which sound.

As a method of maintaining association, the sound data and the electroencephalogram data may be stored as a respective pair in a table, for example. Alternatively, time information indicating a point in time of acquiring the data may be added to each of the sound data and the electroencephalogram data, so that the sound data and the electroencephalogram data are linked on the basis of this time information.

Next, those processes in the above flow which are particularly relevant to the present disclosure, the sound classification process based on attributes (step S30), the accumulation determination process (step S40), and the sound/electroencephalogram data accumulation process (step S60), will be further described in detail with reference to individual flowcharts and the drawings.

FIG. 8 is a diagram showing the detailed processing by the classification section 3, and FIG. 9 is an explanatory diagram of the processing. From within the ambient sounds, the classification section 3 outputs the timing and result of classification of a sound which is eligible for electroencephalogram data accumulation. Among the zones of ambient sounds, which may be various, only a zone which is likely to provide a clear electroencephalographic response needs to be detected. When auditory stimulations occur in succession, it is considered that evoked responses to those sounds are mutually overlaid in the resultant electroencephalogram, and thus analysis of the successive portions of the electroencephalogram will be difficult. Therefore, the inventors basically consider that a timing of obtaining electroencephalogram data which permits relatively easy analysis is the timing with which a silent zone transitions to a non-silent zone. Hereinafter, the flowchart of FIG. 8 will be described, in connection also with FIG. 9 as necessary.

At step S31, the classification section 3 acquires sound data from the acoustic transducer 2. For example, supposing that the classification section 3 receives data from the acoustic transducer 2 every second, the data acquired by the classification section 3 will be the data of sounds which occurred in the latest second (1 second) in the past.

At step S32, based on the sound data in the zone for classification, the classification section 3 determines whether that zone is silent or not. Specifically, if the only sounds that are contained are equal to or below the hearing threshold level, then the zone can be regarded as silent; since this zone does not deserve an assessment, the process proceeds to step S33. On the other hand, if any sound is contained that is above the hearing threshold level, then the zone is considered non-silent, and the process proceeds to step S34.

At step S33, the classification section 3 classifies the zone to be silent, and the process proceeds to step S38.

At step S34, the classification section 3 determines whether all data in the zone for classification was non-silent or not. Specifically, the classification section 3 determines whether sounds which are equal to or above the hearing threshold level was contained across the entire zone for classification or not. If such sounds were contained, the process proceeds to step S35 because there was no change in the sounds; if no such sounds were contained, the process proceeds to step S36 because a transition from a silent zone to a non-silent zone has occurred.

The determination process in step S34 is provided from the following standpoint. There may frequently be situations in daily life which are permeated with some sounds throughout the entire time zone. For example, when music is being played, some sound data will always be obtained, making it impossible to identify which sound an event-related potential is occurring in response to. Therefore, this situation can be regarded as unsuitable for a hearing assessment utilizing an event-related potential. There may be similar problems in other situations where steady noises are occurring, e.g., when one is on a train or in the middle of a crowd, which also hinder an assessment utilizing an event-related potential. For such reasons, not only the process of determining a silent zone at step S32, but also a process of determining a non-silent zone as to whether there was always some sound throughout the entire zone or not at step S34 needs to be made.

On the other hand, one valid situation for making an assessment utilizing an event-related potential is considered to be when a silent state transitions to a non-silent state, because an event-related potential would be evoked in response to the sound(s) in the non-silent state. Therefore, the moment of changing from a silent zone to a non-silent zone must be detected.

At step S35, it is determined that the sound data of the current run is always non-silent and that there was no valid timing for accumulating electroencephalogram data, and the process proceeds to step S38.

At step S36, the classification section 3 detects the timing with which a transition from a silent zone to a non-silent zone occurred. This can be realized by a process of sequentially checking sound data, and identifying a point in time where a certain level or more of data fluctuation (or more specifically, an increase in the sound level) occurred. As a result, the point in time at which a sound was presented to the user is identified, and an event-related potential corresponding to this point in time can be acquired.

At step S37, from the timing identified at step S36, the classification section 3 determines the loudness (sound pressure) of the sound which the user must have heard. The sound pressure is expressed in decibels, for example.

FIG. 9A shows a result of classification when sounds are classified based on sound loudness. By checking which sound receives response in the user's electroencephalogram, a hearing threshold level as to sounds of what loudness are audible, etc., can be assessed. For example, if a sound has a loudness of 20 dB, then that sound is classified into the 20 dB category.

The classification method is not limited to that which is based on sound loudness. For example, sounds may be classified based on the speech sound type or frequency.

FIG. 9B shows an exemplary result of sound classification based on speech sound types. Through a classification based on speech sound types, a speech sound intelligibility assessment as to which speech sound was audible can be made. FIG. 9C shows an exemplary result of sound classification based on the frequency category of an exterior sound. This classification method is a method of recording response to an external sound with respect to the frequency thereof. Some people with hypacusia have poor hearing only at specific frequencies. By recording frequency-by-frequency responses, such symptoms can be effectively determined.

It is not essential to select any single one of the classification methods of FIGS. 9A to 9C. When a given sound is obtained, is may be subjected to simultaneous classifications by the respective methods, because external sounds possess not only sound pressure but also frequency characteristics, and may further possess speech sound information.

Moreover, sound classification may be performed based on a plurality of attributes. For example, through a classification based on both attributes of sound pressure and frequency, it becomes possible to identify a sound pressure which presents hearing difficulty for each frequency in the user's hearing, so that data that particularly deserves collection is made clear from among combinations of frequencies and sound pressures. In a hearing aid adjustment, frequency-by-frequency gains (degrees of sound amplification) finally need to be set; therefore, the response to each sound pressure being recorded in combination with the respective frequency is usable as an effective index of assessment for the hearing aid adjustment.

At step S38, the classification section 3 outputs the determined result of classification. The output is a result of classification which is either one of: classification is impossible (no sounds, no change in sounds); or sound volume. Among these results, based on a result of sound volume classification (i.e., classification was possible), information is sent to the next accumulation determination section 4.

Through such processes, during a period incessantly monitoring ambient sounds, timings for accumulating an electroencephalographic response are determined.

Although this flowchart is directed to an instance of performing a classification based on sound loudness, classification based on speech sound types as shown in FIG. 9B is also possible. In this case, step S37 should read as a process to "determine speech sound type".

Alternatively, a classification based on frequency as shown in FIG. 9C is also possible. In this case, step S37 should read as a process to "determine frequency".

Next, the accumulation determination process shown at step S40 of FIG. 7 will be described in detail. The process of determining the number of times of accumulation is performed by the accumulation determination section 4.

Figures 10, 11A:
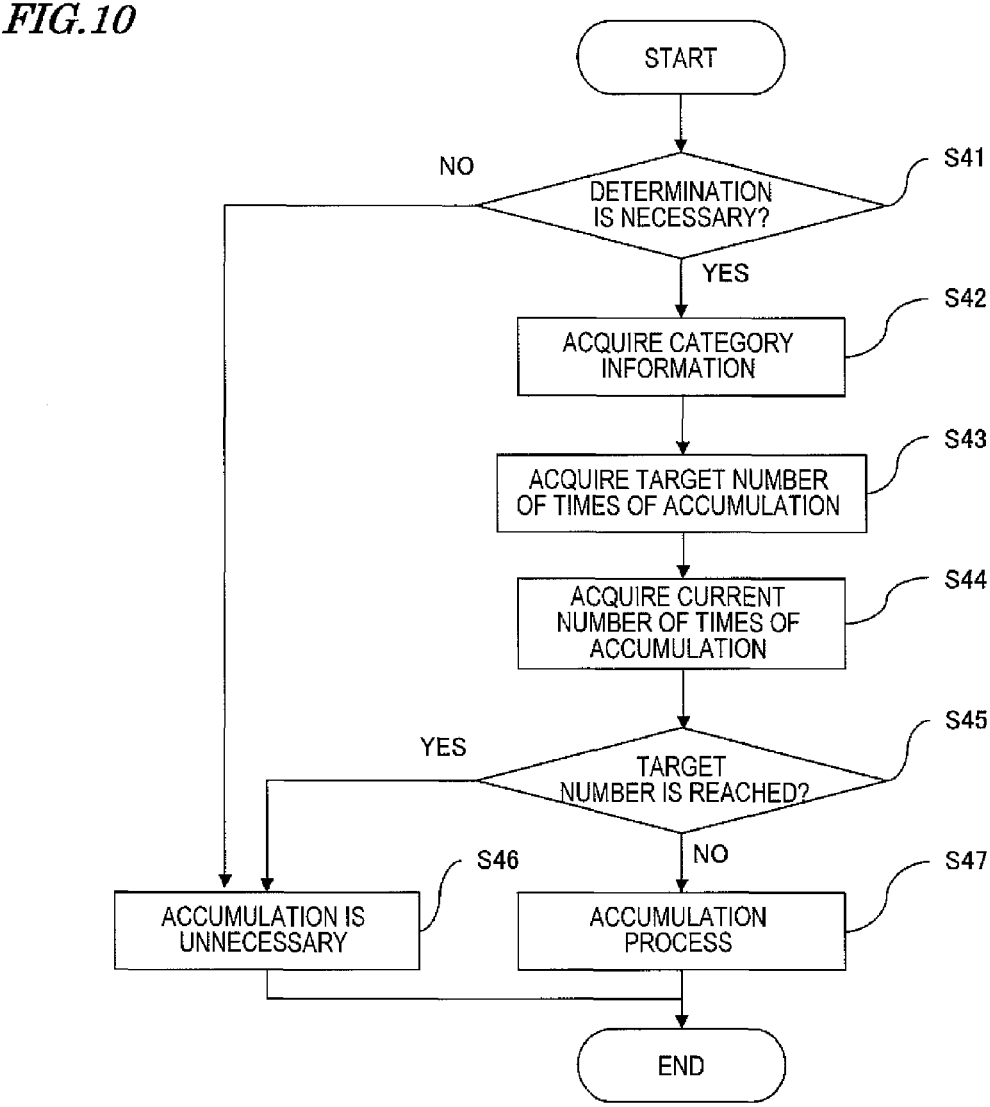
FIG. 10 is a flowchart showing a procedure of processing by an accumulation determination section.
FIG. 11A is a diagram showing an instance of electroencephalogram data accumulation.

FIG. 10 shows a procedure of processing by the accumulation determination section 4. FIGS. 11A and 11B and FIG. 12 illustrate an exemplary data process in the accumulation determination process.

The accumulation determination section 4 retains a predetermined target number of times of accumulation, which is set for each category (attribute). For each category, the accumulation determination section 4 acquires the number of times that data has been accumulated in the accumulation section 6. Then, for the category of a sound which has newly been acquired by the acoustic transducer 2, the accumulation determination section 4 determines whether data accumulation has already been performed up to the predetermined target number of times of accumulation or not, thereby determining whether or not any more accumulation is necessary. In this manner, it is ensured that a necessary amount of electroencephalogram data will be accumulated.

FIG. 11A shows a relationship between the result of sound classification, the target number of times of accumulation, and the current number of accumulations. The result of sound classification corresponds to a category as classified by the classification section 3. The target number of times of accumulation corresponds to an attribute-by-attribute value which is prestored in the accumulation determination section 4. The current number of accumulations corresponds to the number of data that are accumulated in the accumulation section 6. A table file describing the relationship among them is retained in the accumulation determination section 4. For example, the "result of sound classification (category)" pertains to sound loudness, and is divided into nine categories each spanning 10 dB. For each category, a target number of times of accumulation is set. Specific examples may be: for sounds of 0 dB, 20 times of electroencephalogram data accumulation is necessary; for sounds of 80 dB, 10 times of electroencephalogram data accumulation is necessary; and so on. These values are determined based on the characteristics (the level of the electroencephalogram component to be assessed) of the electroencephalogram and the required assessment accuracy. For example, in the case of performing assessment based on N1 components in response to sounds, the target number of times of accumulation may be set to about "10 times" for loud sounds because a sufficiently large N1 component is expectable, whereas the target number of times of accumulation may be set to about "20 times" for softer sounds. In the case where the user's hearing threshold level is expected to be in the neighborhood of 20 dB or 30 dB, the number of times of accumulation may be further increased to 40 times for an accurate determination in those neighborhoods. Furthermore, the current number of accumulations is also indicated in the same row. This number of times represents how much accumulation has been made since the user put on the electroencephalogram recording apparatus 100.

FIG. 11B (a) to (c) show examples of setting target numbers of times of accumulation. Setting of the target number of times of accumulation is performed by the accumulation determination section 4.

In FIG. 11B, "○" symbols indicate the relationship between sound pressure values respectively corresponding to the plurality of categories as exemplified by the "result of sound classification" in FIG. 11A and the target number of times of accumulation defined for each sound pressure value. In each graph of FIG. 11B, a line connecting the "○" symbols is indicated in order to facilitate the understanding of the relationship (profile) between sound pressures and target numbers of times of accumulation. The actually-measured sound pressure fits into each corresponding category. For example, if the measured sound pressure is between 35 dB and 44 dB, the sound will be classified into the 40 dB category.

FIG. 11B(a) shows an example setting where the necessary target number of times of accumulation is linearly decreased as the sound pressure increases. As has been described with reference to FIG. 1, depending on the sound pressure level, the N1 component an event-related potential which is evoked by that sound will change, and the necessary number of summations will also vary. Therefore, such a setting may work when it is desirable to analyze the N1 amplitude while minimizing the number of times of accumulation for each sound pressure, but with the same accuracy.

FIG. 11B(b) shows an example setting of target numbers of times of accumulation in the case where the HTL (hearing threshold level) of the user is already somewhat expectable. As mentioned earlier, the N1 component response becomes particularly small near a sound pressure at which the HTL is expected to exist. In order to check for an N1 component response near that sound pressure, a particularly large number of summations is needed. Therefore, a large number of summations is set only for the portion where the HTL is expected to exist, while otherwise the number of accumulations is basically small. Such is the concept behind the settings of target numbers of times of accumulation in FIG. 11B(a) and (b).

FIG. 11B(c) shows an example where the user's HTL is unknown and the exact HTL value needs to be found, thus resulting in a distribution of target numbers of accumulations for allowing responses in the range where the HTL is expected to exist to be acquired with a particular focus. Thus, it is necessary to set a target number of times of accumulation depending on what is to be determined.

In summary, according to FIG. 11B(a), the accumulation determination section 4 designates a larger target number of times of accumulation as the sound pressure value of the category decreases, and designates a linearly smaller target number of times of accumulation as the sound pressure value of the category increases. The category into which sounds of the smallest expectable value are to be classified receives the largest target number of times of accumulation, while the target number of times of accumulation is smaller in any other category (i.e., other categories into which sounds that are louder than the smallest-value sound are classified).

On the other hand, according to FIG. 11B(b) and (c), the accumulation determination section 4 sets the target number of times of accumulation so as to be largest at/within a value or range where the HTL is expected to exist. A common target number of times of accumulation may be set for two or more adjacent categories. The target number of times of accumulation may be greatly decreased in any sound pressure range outside the value or range where the HTL is expected to exist.

FIG. 10 is again referred to. At step S41 in FIG. 10, the accumulation determination section 4 receives an output result from the classification section 3, and determines the presence or absence of a result of classification. If the result of classification is absent, i.e., when there is no sounds or no change in sounds, then the process proceeds to step S46; if any result of classification exists, then the process proceeds to step S42.

At step S42, the accumulation determination section acquires category information of the result of classification. If classification is made based on sound loudness, the category information is loudness of the current ambient sound (dB). In FIG. 11A, this corresponds to the information which is indicated in the column of the result of sound classification.

At step S43, from the table (FIG. 11A) which is stored in the accumulation determination section 4, the accumulation determination section 4 acquires the target number of times of accumulation for the category of the current run. For example, if the category is 20 dB, the accumulation determination section 4 acquires "40 times" as the target number of times of accumulation, by referring to the table.

At step S44, the accumulation determination section acquires the current number of accumulations for the category of the current run, from its internally-stored table (FIG. 11A). For instance, in the example of FIG. 11A, the current number of accumulations indicated for 30 dB, i.e., 20 times, is acquired.

At step S45, the accumulation determination section 4 determines whether the current number of accumulations is sufficient in view of the target value. If the number of accumulations has reached the target value, the process proceeds to step S46; if the number of accumulations has not reached the target value, the process proceeds to step S47. In the example of FIG. 11A, the current value is 20 times, as opposed to the targeted 50 times, and therefore the accumulation determination section 4 determines that accumulation is necessary.

At step S46, the accumulation determination section 4 determines that accumulation is unnecessary. Since no more accumulation is necessary, a message that data accumulation has been completed for the category may be presented in the form of an audio or the like. Moreover, if the target amount has been attained but it is still desired to collect the most recent response of the user, the accumulation determination section 4 may perform at this step a process of destroying data that was accumulated at the oldest timing and replacing it with new data.

If the target amount has been attained for all categories, that information may be presented by the device, thus conveying the fact as to when collection of information was completed. Since the completion of information accumulation is conveyed to the user or an expert at the shop, it is ensured that the assessment device is worn only for a necessary and sufficient time.

At step S47, the accumulation determination section 4 determines that accumulation is necessary, and operates to perform an accumulation process. Specifically, the accumulation determination section 4 refers to the point of occurrence of the sound data to be accumulated, acquires electroencephalogram data (event-related potential) corresponding to that point of occurrence from the electroencephalogram measurement section 5, accumulates it in the accumulation section 6, and updates the current number of accumulations in the table of FIG. 11A.

FIG. 12 shows a flow of processing for sound data and electroencephalogram data. The data of an audio 11 which is collected by the acoustic transducer 2 is classified by the classification section 3, whereby Starting Point 1 and a sound volume 30 dB of the current sound are determined. Based on this output from the classification section 3, the accumulation determination section 4 compares the target number of times of accumulation (50 times) against the current number of accumulations (20 times) by referring to a table 13, and thus determines that the sound data and electroencephalogram data are to be accumulated in this situation. As a result, within the data of an electroencephalogram 12 being output from the electroencephalogram measurement section 5, the accumulation section 6 acquires data of an electroencephalogram (event-related potential) 15 corresponding to Starting Point 1, and accumulates the sound data and electroencephalogram data which have been output from the electroencephalogram measurement section 5 based on an instruction from the accumulation determination section 4, the sound data and the electroencephalogram data being kept in association. Note that, the data length is −100 milliseconds to 600 milliseconds based on Starting Point 1.

Through the above processes, electroencephalogram data can be accumulated up to a number of times that is necessary for hearing ability assessment.

With this construction, by comparing the attribute category of the sound that is needed for the electroencephalogram-based hearing assessment against the target data amount which is set for each category, it becomes possible to accumulate a necessary and sufficient amount of data even under limitations of recording capacity and power consumption.

Through the above procedure, paired data of ambient sound data and electroencephalogram data are accumulated in the accumulation section 6.

Next, it will be described how accumulated data is brought into a hearing aid shop to be used by an expert.

FIG. 13A shows the hardware construction of a PC 200 which is installed at a hearing aid shop. The PC 200 includes a CPU 30, a memory 31, a graphics controller 32, and a communications controller 33. These are interconnected via a bus 34, so that data exchange among them is possible.

The CPU 30 executes a computer program 35 which is stored in the memory 31. In accordance with the computer program 35, the PC 200 performs the processes described below. The computer program 35 is hearing aid fitting software, or a software module which defines a part thereof. Hearing aid fitting software is a piece of software which is capable of referencing and setting of internal parameter values of a hearing aid, and which also allows their adjustments to be controlled by an expert on a displayed screen of the fitting software. The assessment process of accumulated data according to the present disclosure can be implemented as an extended function of the fitting software, with the following expected usages: assessment results may be displayed on the screen for confirmation by the expert; the assessment results may be automatically reflected on the fitting parameter setting; and so on.

In accordance with an instruction from the CPU 30, the graphics controller 32 generates a video signal, and outputs it to a monitor (not shown). The monitor displays this video signal.

Moreover, when a memory card 36 is mounted in a memory card slot (not shown) of the PC 200, the communications controller 33 writes data to, or reads data from, the memory card 36. In the present embodiment, it is assumed that the memory card 36 is the memory card which is a part of the accumulation section 6 of the electroencephalogram recording apparatus 100. In accordance with an instruction from the CPU 30, the communications controller 33 reads the sound data and electroencephalogram data that are accumulated in the memory card 36.

Note that the communications controller 33 may be a communications controller to be connected to a hard disk drive or an optical disk drive for controlling an interface (e.g., USB), or a network controller which receives data over a network. Alternatively, the communications controller 33 may be directly connected to the electroencephalogram recording apparatus 100 and refer to accumulation results in the accumulation section 6.

Note that the above construction may be implemented as a single processor or circuit. Alternatively, each element included in the PC 200 may be implemented as one processor or circuit; or two or more of them may be implemented as one processor or circuit.

FIG. 13B is a flowchart showing the procedure of a process of converting accumulated data into hearing assessment results. FIG. 14 shows an exemplary conversion process from an accumulation result (a) to a hearing assessment (b) at a hearing aid shop.

At step S61 in FIG. 13B, via the communications controller 33, the CPU 30 of the PC 200 acquires category information from the memory card 36. Category information may be defined in terms of loudness of the ambient sounds, in increments of 10 dB from 0 dB to 100 dB, for example. A result of classification 21 in FIG. 14 shows an example thereof.

At step S62, the CPU 30 acquires the electroencephalographic information which is recorded in the aforementioned category. For example, the number of accumulations 23 corresponding to 30 dB in FIG. 14 is 40 times, and therefore 40 event-related potential waveforms are obtained from the electroencephalogram data 24.

At step S63, the CPU 30 derives an arithmetic mean waveform from the electroencephalographic information obtained at step S62. While each single event-related potential waveform is considerably affected by noises, taking an arithmetic mean allows only the components that needed for the assessment to be extracted.

At step S64, the CPU 30 calculates the amplitude of the component of interest from the arithmetic mean waveform obtained at step S63. For example, in the case of an N1 component assessment, the amplitude of a waveform having a negative peak in the neighborhood of 100 milliseconds is calculated.

At step S65, for each sound volume category, the CPU 30 stores the amplitude 26 calculated at step S64 as well as the assessment result corresponding to that amplitude. Among the expected instances of FIG. 14, for example, the ERP average amplitude 26 for the 20 dB category is 0 µV, indicative that no response is observed. Therefore, the CPU 30 makes an assessment that the sound is not being heard. On the other hand, the average amplitude 26 is 1.2 µV for the dB category. Therefore, the CPU 30 makes an assessment that response is observed, although little.

At step S66, the CPU 30 determines whether the assessment has been completed for all categories for assessment. If there is any undetermined category left, the process proceeds to step S61; if all assessments have been completed, the process is ended.

Through such processes, an assessment result based on the electroencephalogram is generated corresponding to each category. Based on these assessment results, in FIG. 14, the hearing threshold level 28 can be assessed to be 30 dB, at which the event-related potential response begins to appear. By checking the responses to the respective sounds to see when the average amplitude ceases to increase, it is also possible to assess annoying sounds. Note that an "annoying sound" means a sound which is too loud to the user, e.g., a sound so loud that the user feels uncomfortable. Since the perception of uncomfortableness varies from user to user, it would not be appropriate to universally define an "annoying sound".

The present embodiment illustrates a case where the attribute which is subjected to classification by the aforementioned classification section 3 is the loudness of an external sound. However, the attribute may be a speech sound type; in that case, instead of responses to sound loudness, responses to speech sounds are examined, thereby enabling a speech sound intelligibility assessment. The assessments of speech sounds may be made in a collective manner for each consonant group as shown in FIG. 9, rather than making an assessment for each single sound. From the standpoint of sound data, the same consonant will lead to the same rise of sound data, and thus there is significance in obtaining an event-related potential with respect to the rise portion. For example, in order to determine the intensity of a consonant emphasis process in a hearing aid, accumulation for each consonant group will be important.

Determination of the attribute of a speech sound is realized through signal processing such as speech sound recognition or consonant group recognition. Various techniques have hitherto been proposed for speech sound recognition, and are available to the general public. These are techniques of extracting some characteristic amounts from an original audio signal via frequency analysis or the like, and based on these characteristic amounts, determining the speech sound type or consonant type by a previously designated determination method. Any such recognition technique can be independently introduced to the construction of the present disclosure.

The present embodiment has illustrated a method of consecutively storing pairs of sound signals and electroencephalogram signals. When there are limitations of storage capacity, the sound signals may not be accumulated in the form of waveforms, but stored only as category information indicative of results of classification of sound signals, and the electroencephalogram data may not be accumulated in the form of waveforms, but stored only as arithmetic mean results for the respective categories. In this case, the data amount to be stored would be one arithmetic-meaned event-related potential for each category.

(Embodiment 2)

The present embodiment will illustrate an electroencephalogram recording apparatus which, in addition to the construction of Embodiment 1, includes a construction for allowing an electroencephalogram assessment to be made in the apparatus itself, and which modifies the criterion for determination of accumulation in accordance with the result thereof.

It is known that the state of hearing of a user who needs a hearing aid admits greater variation than that of a person with normal hearing. Therefore, the number of times of accumulation that is originally defined for the sound loudness may not always be a guarantee that necessary data will be sufficiently accumulated. Therefore, once a sizable amount of electroencephalogram data has been accumulated, a simplified assessment of the electroencephalogram may be performed, and by modifying the data accumulation amount by using the result thereof, a user with various states of hearing can be dealt with. Without this function, on the other hand, insufficiency of data will only be known when the accumulate data is confirmed at a hearing aid shop, in which case additional data collection will be necessitated with a readjusted data accumulation amount.

FIG. 15 shows the construction of an electroencephalogram recording apparatus 105 according to the present embodiment. Component elements shown in FIG. 15 having the same functions as those in Embodiment 1 (FIG. 3) will be denoted by the same reference numerals, and the descriptions thereof will be omitted.

One difference of the electroencephalogram recording apparatus 105 of the present embodiment from the electroencephalogram recording apparatus 100 according to Embodiment 1 is that an electroencephalogram analysis section 7 is additionally introduced. Hereinafter, a detailed operation of the electroencephalogram analysis section 7 will mainly be described.

FIG. 16 is a flowchart showing a procedure of processing by the electroencephalogram recording apparatus 105 of the present embodiment. Steps S20 to S60, which respectively receive the same reference numerals as those in FIG. 6, define similar processes to those shown in the flowchart of FIG. 6, and the detailed descriptions thereof will be omitted.

At step S70, the electroencephalogram analysis section 7 conducts a simplified hearing determination by analyzing the accumulated electroencephalograms, and, as necessary, modifies the determination criterion used by the accumulation determination section 4. The hearing determination is a process of analyzing accumulated electroencephalograms to determine whether the user is hearing the sounds at all. Modification of the determination criterion would mean, specifically, increasing or decreasing the target number of times of accumulation.

Through this process, more relevant data for an electroencephalogram-based hearing assessment can be efficiently collected.

Next, within the above flow, the details of the processes of the electroencephalogram analysis section 7 will be described with reference to individual flowcharts and the drawings.

FIG. 17 shows details of the processing by the electroencephalogram analysis section. FIG. 18 shows an exemplary process of modifying the determination criterion in accordance with the processing by the electroencephalogram analysis section 7. Hereinafter, the flowchart of FIG. 17 will be described, in connection also with FIG. 18 as necessary. It is assumed that the electroencephalogram analysis section 7 according to the present embodiment is activated only when data is newly added.

At step S71 in FIG. 17, the electroencephalogram analysis section 7 acquires category information as a result of classification from the classification section 3.

At step S72, the electroencephalogram analysis section 7 acquires electroencephalographic information corresponding to the category. As used herein, "electroencephalographic information" means the target number of times of accumulation for the category, the current number of times of accumulation, and the accumulated event-related potential waveforms.

At step S73, the electroencephalogram analysis section 7 determines whether the target number of times of accumulation is to be adjusted or not. This is because, in order for the electroencephalogram analysis section 7 to make an adjustment, it is necessary that a sizable amount of electroencephalogram data has been accumulated in the accumulation section 6. If there is less than enough accumulated electroencephalogram data, it is likely that a correct assessment may not be made. A "sizable amount" may be known by checking whether the accumulated electroencephalogram data corresponds to a half or more of the target number of times of accumulation, for example.

The electroencephalogram analysis section 7 determines how much electroencephalogram data has been accumulated in the accumulation section 6. If it is determined that an adjustment is to be made, the process proceeds to step S74; if it is determined that adjustment is not to be made, the process of the electroencephalogram analysis section 7 is ended.

At step S74, the electroencephalogram analysis section 7 calculates an arithmetic mean waveform by using the acquired electroencephalogram data alone.

At step S75, the electroencephalogram analysis section 7 calculates the amplitude of a component of interest from the arithmetic mean waveform calculated at step S75. For example, in the case of assessing an N1 component, the amplitude of a waveform having a negative peak in the neighborhood of 100 milliseconds is calculated.

At step S76, the electroencephalogram analysis section 7 determines whether the amplitude level calculated at step S75 is equal to an expected amplitude or not. The expected amplitude is the amplitude of an electroencephalogram, as previously expected, to be evoked in a standard user. This allows the necessary amount of electroencephalogram data to be adjusted according to the hearing of each user. If the amplitude is smaller than expected, the process proceeds to step S77; if the amplitude is essentially equal to the expected value, the process proceeds to step S78; if the amplitude is greater than expected, the process proceeds to step S79.

Step S77 is a process to occur when the amplitude of the event-related potential is determined as smaller than expected. Therefore, in order to perform a more accurate hearing assessment, the target number of times of accumulation for the category of the current run is increased, and thereafter the process is ended. For example, if the electroencephalogram analysis section 7 assesses the electroencephalogram component to determine that the hearing threshold level is near 20 dB, the target number of times is increased, and thereafter the process is ended.

Step S78 is a process to occur when the amplitude of the event-related potential is determined as essentially equal to the expected value. Therefore, the process is ended without changing the target number of times of accumulation.

Step S79 is a process to occur when the amplitude of the event-related potential is determined as greater than expected. Therefore, based on the judgment that a sufficiently accurate hearing assessment can be made with a smaller number of data, the target number of times of accumulation for the category of the current run is decreased, and thereafter the process is ended.

With reference to FIG. 18, an example of this process will be illustrated where the process proceeds to S77 based on a result of determination at step S76. Assuming that an N1 amplitude for a sound pressure of 20 dB is calculated by using the currently accumulated data, for example, if it is smaller than the expected waveform, a determination is going to be made as to whether an N1 component amplitude is marginally observed (i.e., the hearing threshold level) or not observed at all (i.e., smaller than the threshold) for the 20 dB sound pressure. Therefore, what would be necessary is to make a determination after reducing noise influences by increasing the number of times of accumulation. For this reason, although the target number of times of accumulation originally defined for the current 20 dB category was 40 times, the accumulation determination section 4 adjusts the target number of times of accumulation up to 50 times, in order to enable a more accurate assessment. When sounds are soft, the data will concentrate particularly near the hearing threshold level, and thus data of this portion needs to be particularly carefully collected, making it necessary to perform such a process.

If, on the other hand, the process proceeds to step S79 based on a result of determination at step S76, the accumulation determination section 4 may adjust the target number of times of accumulation so as to become smaller. Assuming that an N1 component amplitude for the sound pressure category of 30 dB is calculated, for example, if it is greater than the expected waveform, it can be judged that a sufficiently accurate hearing assessment can still be made with a smaller number of data because a sufficient N1 component response is being observed (i.e., evidently above the hearing threshold level) for the 30 dB sound pressure category. The accumulation determination section 4 may decrease the originally-defined target number of times of accumulation (i.e., 40 times) to 30 times. In this case, there is an increased likelihood that the hearing threshold level exists at a smaller sound pressure than this; therefore, the target number of times of accumulation may be increased for e.g. the 20 dB and/or 10 dB categories for more accurate determination (not shown), even though the number of times is decrease for the 30 dB category.

The present embodiment illustrates an example where the target value for the loudness of a given ambient sound(s) is changed as a result of analyzing the user's hearing in the electroencephalogram analysis section 7. Furthermore, the hearing threshold level, the uncomfortableness threshold value, and the like of the user may be estimated, and the target number of times of accumulation may be changed based on their values. For example, if an estimated value of the user's hearing threshold level is corrected, a large target number of times of accumulation may be designated only near the hearing threshold level, as shown in FIG. 11B(b).

If the user is a person suffering from hypacusia, there may be cases where specific frequencies are difficult to hear. Therefore, assuming a frequency-by-frequency data accumulation as shown in FIG. 9C, the data accumulation amount for each such category may be modified. Fourier transform or the like can be employed for the Frequency analysis. If the result of electroencephalogram analysis indicates that the response is weak only at a specific frequency, the data accumulation amount for that frequency may be increased to enable more accurate assessment. Thus, valid data can be acquired in the hearing aid adjustments for various types of people suffering from hypacusia.

Through these processes, a simplified version of hearing assessment from data accumulation results is performed, prior to visiting a hearing aid shop. As a result, it becomes possible to determine which category needs more intensive collection of ambient sound data and electroencephalogram data, thus enabling accumulation of necessary and sufficient data. This precludes the expert at a hearing aid shop from pointing out insufficiency of data collection, which saves the trouble of data collection and any more visits to the hearing aid shop.

The present embodiment has illustrated instances of enabling efficient data accumulation. Upon completion of sufficient data accumulation, if data exchanges via communications are possible with the hearing aid shop, a remote fitting would also become possible. The conventional reasons why a user must visit a hearing aid shop are: (1) a hearing assessment can only be made at the shopfront; and (2) a hearing aid adjustment can only be made at the shopfront. However, once efficient data accumulation is realized as illustrated in the present embodiment, the hearing aid shop may initially ask the user to bring home the hearing aid, receive an assessment result by the electroencephalogram recording apparatus 105 via communications, and after an expert determines an appropriate setting value for the hearing aid based on that result, allow the user to have that setting value downloaded to the hearing aid at hand, again via communications. Thus, a remote hearing aid adjustment is possible.

(Embodiment 3)

The present embodiment contemplates a case where an expert's fitting at a hearing aid shop is not performed, but a data recording function and an assessment function are incorporated into the hearing aid main body, so that automatic adjustments are made inside the hearing aid.

FIG. 19 shows the construction of a hearing aid 110 according to the present embodiment. The hearing aid 110 includes the electroencephalogram recording apparatus 100 according to Embodiment 1, for example, and a hearing aid section 101. In FIG. 19, component elements identical those in FIG. 3 will be denoted by like reference numerals, and the descriptions thereof will be omitted. In addition to the construction of Embodiment 1, the construction of the present embodiment includes a hearing assessment section 8 and the hearing aid section 101.

The hearing assessment section 8 performs a hearing assessment by using data in the accumulation section 6. It basically performs the process of converting accumulate data into an assessment result which was described with reference to FIG. 13B and FIG. 14, and also serves to determine a final adjustment parameter for the hearing aid, which would otherwise be done by an expert. As a result, without requiring an expert, a hearing aid adjustment can be made.

The illustrated hearing aid section 101 has the construction of a generic hearing aid. In the hearing aid section 101, an acoustic transducer 101a acquires an ambient sound; an acoustic aiding processing section 101b applies an acoustic aiding process to the ambient sound; and an output section 101c presents a sound which is obtained through the acoustic aiding process to the user. The acoustic aiding processing section 101b accepts an external control signal, and upon receiving a parameter as adjusted by the hearing assessment section 8, allows it to be reflected in the acoustic aiding process by the hearing aid section 101.

Through such processes, the data in the electroencephalogram recording apparatus 100 is directly provided to the hearing aid as it is.

FIG. 20, in (a) and (b), illustrates a scene of use of the system. FIG. 20(a) illustrates an exemplary outer construction of a hearing aid 110 in which the electroencephalogram recording apparatus 100 and the hearing aid section 101 are integrated, and FIG. 20(b) shows an example of wearing it. The user is wearing the hearing aid 110 on his or her ear. The electroencephalogram recording apparatus 100 in FIG. 20 is embedded in the hearing aid 101, such that the acoustic transducer 2 and the acoustic transducer 101a of the hearing aid are really a single element. The electroencephalogram measurement section 5 includes electrodes 5a and a biometric amplifier 5b, the electrodes being disposed outside the hearing aid so as to come in contact with the head when the hearing aid is worn. Electroencephalogram measurement occurs as a potential difference between at least two electrodes that are attached on the head and its neighborhood is measured. In this instance, the electrodes are disposed at portions where the hearing aid main body comes in contact with an ear of the user. Although an electroencephalogram which is measurable in the ear neighborhood may have different waveforms or characteristic features from those of an electroencephalogram which is measurable at the parietal, an assessment method can be constructed so as to be adapted to an electroencephalogram which is measured in the ear neighborhood.

In these days, there are cases where hearing aids are concurrently worn on both ears for improved performance and comfort in use, in which case an electroencephalogram measurement can be performed based on a potential difference between both ears, whereby encephalic activities can be more easily measured.

Effective electrode positions may be found within the ear(s). The inside of an ear provides a particular ease for fixation, and permits sustained contact in spite of body motions; therefore, it would be effective to place a ground electrode and/or a reference electrode there.

By incorporating the electroencephalogram recording apparatus 100 into the hearing aid section 101, assessment results can be automatically reflected on the hearing aid. Even when the user's hearing changes over time, an optimum hearing via the hearing aid will be maintained so long as sound data and electroencephalogram data are consecutively updated.

The electroencephalogram recording apparatus according to the present disclosure classifies ambient sounds into a category, and accumulates electroencephalogram data which is suitable for that category, thus being useful for the adjustment of a hearing aid at a hearing aid shop. When a person with normal hearing is involved, the electroencephalogram recording apparatus according to the present disclosure can be used for the assessment of ambient sounds. For example, it is applicable to collection of fundamental data, e.g., sound quality assessments of television sets or stereo sets, acoustic environment assessments at train stations or public facilities based on user feelings, and noise assessments at factories or the like.

While the present invention has been described with respect to exemplary embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. An electroencephalogram recording apparatus comprising:
    an acoustic transducer configured to collect external sounds to generate sound data;
    an electroencephalograph which measures an electroencephalogram of a user to generate electroencephalogram data;
    one or more memories; and
    circuitry which in operation is configured to:
    classify a sound collected by the acoustic transducer into one of a plurality of predetermined categories concerning a sound pressure of the sound;
    determine whether or not to record the electroencephalogram data based on whether a number of times of data accumulation has reached a predetermined target value for the category into which the sound is classified; and
    accumulate the electroencephalogram data and the sound data in association by recording the electroencephalogram data and the sound data in the one or more memories if the circuitry determines that the electroencephalogram data is to be recorded,
    wherein, the circuitry is configured to designate the target value of the number of times of data accumulation for each category such that among the plurality of categories, a first value is designated as the target value for a first category into which sounds of an expected minimum value of sound pressure are classified, and a second value is designated as the target value for a second category into which any sound having a sound pressure value greater than the minimum value is classified, the first value being set equal to or greater than the second value.

2. The electroencephalogram recording apparatus of claim 1, wherein, the circuitry further is configured to:
    determine that the electroencephalogram data is to be recorded when the number of times of data accumulation in the category into which the sound is classified is smaller than the predetermined target value; and
    determine that the electroencephalogram data is not to be recorded when the number of times of data accumulation in the category into which the sound is classified is equal to or greater than the predetermined target value.

3. The electroencephalogram recording apparatus of claim 1, wherein, when the circuitry determines that the electroencephalogram data is to be recorded, the circuitry accumulates the sound and an electroencephalogram measured at a point in time at which the sound is collected, the sound and an electroencephalogram being kept in association.

4. The electroencephalogram recording apparatus of claim 1, wherein, when an electroencephalogram component of interest in the electroencephalogram changes with the sound pressure value, the circuitry varies the target value in accordance with a level of the sound pressure value.

5. The electroencephalogram recording apparatus of claim 4, wherein the circuitry designates an increasingly larger target value for a category into which sounds of increasingly smaller sound pressure values are classified.

6. The electroencephalogram recording apparatus of claim 4, wherein the circuitry designates an increasingly smaller target value for a category into which sounds of increasingly larger sound pressure values are classified.

7. The electroencephalogram recording apparatus of claim 4, wherein the circuitry designates an increasingly and linearly smaller target value for a category into which sounds of increasingly larger sound pressure values are classified.

8. The electroencephalogram recording apparatus of claim 4, wherein the circuitry designates the first value as a common target value for two or more adjacent categories including the first category.

9. The electroencephalogram recording apparatus of claim 1, wherein the circuitry further is configured to analyze the electroencephalogram or electroencephalograms accumulated in the one or more memories to determine whether the user has heard the sound or not, wherein,
    the circuitry increases the target value for a category corresponding to any sound determined as not being heard by the user.

10. The electroencephalogram recording apparatus of claim 9, wherein the circuitry analyzes an electroencephalogram response from the recorded data to estimate an uncomfortableness threshold value at which the user has felt uncomfortable, and changes the first value based on the uncomfortableness threshold value.

11. The electroencephalogram recording apparatus of claim 9, wherein, the circuitry further is configured to:
    classify the sound into one of a plurality of predetermined categories concerning the sound pressure and a frequency of the sound; and
    identify a frequency which is difficult for the user to hear, and increases the target value for a category corresponding to the frequency.

12. The electroencephalogram recording apparatus of claim 1, wherein the circuitry accumulates category information as a result of classification of the sound data, and accumulates an arithmetic mean of the electroencephalogram data for each category.

13. The electroencephalogram recording apparatus of claim 1, wherein the electroencephalograph measures the electroencephalogram by using a reference electrode and a ground electrode, at least one of the reference electrode and a ground electrode being configured to be placed in an ear.

14. An electroencephalogram recording apparatus comprising:
an acoustic transducer configured to collect external sounds;
an electroencephalograph which measures an electroencephalogram of a user;
one or more memories; and
circuitry which in operation is configured to:
classify a sound collected by the acoustic transducer into one of a plurality of predetermined categories based on a sound pressure of the sound;
determine whether or not to record the electroencephalogram measured by the electroencephalograph based on whether a number of times of data accumulation has reached a predetermined target value for the category into which the sound is classified; and
accumulate in association the electroencephalogram and the sound for each category by recording electroencephalogram data and the sound data in the one or more memories if the circuitry determines that the electroencephalogram data is to be recorded, wherein,
the circuitry is configured to designate a target value of the number of times of data accumulation for each of the plurality of categories; and
the circuitry designates an increasingly larger target value for a category of an increasingly smaller sound pressure.

15. A hearing aid comprising:
the electroencephalogram recording apparatus of claim 1; and
circuitry which in operation is configured to:
perform a hearing assessment from data accumulated in the one or more memories;
perform a different acoustic aiding process depending on an output result from the hearing assessment; and
present a result of the acoustic aiding process to the user in the form of a sound.

16. An electroencephalogram recording method comprising the steps of:
collecting external sounds with an acoustic transducer to generate sound data;
measuring an electroencephalogram of a user with an electroencephalograph to generate electroencephalogram data; and
operating circuitry to perform the steps of:
classifying a sound collected by the step of collecting external sounds into one of a plurality of predetermined categories concerning a sound pressure of the sound;
determining whether the electroencephalogram data is to be recorded or not based on whether a number of times of data accumulation has reached a predetermined target value for the category into which the sound is classified; and
accumulating the electroencephalogram data and the sound data in association by recording the electroencephalogram data and the sound data in the one or more memories if the determining step determines that the electroencephalogram data is to be recorded, wherein,
a target value of the number of times of data accumulation is designated for each category such that among the plurality of categories, a first value is designated as the target value for a first category into which sounds of an expected minimum value of sound pressure are classified, and a second value is designated as the target value for a second category into which any sound having a sound pressure value greater than the minimum value is classified, the first value being set equal to or greater than the second value when executing the accumulating step.

17. A non-transitory computer-readable medium storing a computer program to be executed by a computer mounted in an electroencephalogram recording apparatus,
wherein the computer program causes the computer in the electroencephalogram recording apparatus to execute the steps of:
generating sound data of collected external sounds;
acquiring electroencephalogram data measured of a user;
classifying a collected sound into one of a plurality of predetermined categories concerning a sound pressure of the sound;
determining whether the electroencephalogram data is to be recorded or not based on whether a number of times of data accumulation has reached a predetermined target value for the category into which the sound is classified; and
accumulating the electroencephalogram data and the sound data in association by recording the electroencephalogram data and the sound data in one or more memories if the determining step determines that the electroencephalogram data is to be recorded, wherein,
a target value of the number of times of data accumulation is designated for each category such that among the plurality of categories, a first value is designated as the target value for a first category into which sounds of an expected minimum value of sound pressure are classified, and a second value is designated as the target value for a second category into which any sound having a sound pressure value greater than the minimum value is classified, the first value being set equal to or greater than the second value when executing the accumulating step.

* * * * *